US008110587B2

(12) United States Patent
Dumas et al.

(10) Patent No.: US 8,110,587 B2
(45) Date of Patent: Feb. 7, 2012

(54) ARYL UREAS AS KINASE INHIBITORS

(75) Inventors: Jacques Dumas, Orange, CT (US);
William J. Scott, Guilford, CT (US);
Bernd Riedl, Wuppertal (DE);
Du-Schieng Chien, Guilford, CT (US);
Ala Nassar, Milford, CT (US); Wendy Lee, Hamden, CT (US); Susan Bjorge, Milford, CT (US); Laszlo Musza, New Haven County, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 10/361,859

(22) Filed: Feb. 11, 2003

(65) Prior Publication Data
US 2003/0216446 A1    Nov. 20, 2003

Related U.S. Application Data

(60) Provisional application No. 60/354,937, filed on Feb. 11, 2002.

(51) Int. Cl.
*A61K 31/44* (2006.01)
*C07D 211/72* (2006.01)
*C07D 211/92* (2006.01)

(52) U.S. Cl. .................. 514/351; 546/290; 546/300

(58) Field of Classification Search .................. 514/351; 546/290, 300
See application file for complete search history.

(56) References Cited

U.S. PATENT DOCUMENTS

| 502,504 | A | 8/1893 | Thoms |
| 1,792,156 | A | 12/1929 | Fitzky |
| 2,093,265 | A | 9/1937 | Coffey et al. |
| 2,046,375 | A | 7/1938 | Goldstein et al. |
| 2,288,422 | A | 8/1942 | Rohm et al. |
| 2,649,476 | A | 8/1953 | Martin |
| 2,683,082 | A | 7/1954 | Hill et al. |
| 2,722,544 | A | 11/1955 | Martin |
| 2,745,874 | A | 5/1956 | Schetty et al. |
| 2,781,330 | A | 2/1957 | Downey |
| 2,797,214 | A | 6/1957 | Bossard |
| 2,867,659 | A | 1/1959 | Model et al. |
| 2,877,268 | A | 3/1959 | Applegath et al. |
| 2,960,488 | A | 11/1960 | Tamblyn et al. |
| 2,973,386 | A | 2/1961 | Weldon |
| 3,151,023 | A | 9/1964 | Martin |
| 3,200,035 | A | 8/1965 | Martin et al. |
| 3,230,141 | A | 1/1966 | Frick et al. |
| 3,424,760 | A | 1/1969 | Helsley et al. |
| 3,424,761 | A | 1/1969 | Helsley et al. |
| 3,424,762 | A | 1/1969 | Helsley et al. |
| 3,547,940 | A | 12/1970 | Brantley |
| 3,646,059 | A | 2/1972 | Brantley |
| 3,689,550 | A | 9/1972 | Schellenbaum et al. |
| 3,743,498 | A | 7/1973 | Brantley |
| 3,754,887 | A | 8/1973 | Brantley |
| 3,823,161 | A | 7/1974 | Lesser |
| 3,828,001 | A | 8/1974 | Broad et al. |
| 3,860,645 | A | 1/1975 | Nikawitz |
| 3,990,879 | A | 11/1976 | Soper |
| 4,001,256 | A | 1/1977 | Callahan et al. |
| 4,009,847 | A | 3/1977 | Aldrich et al. |
| 4,042,372 | A | 8/1977 | Harper |
| 4,062,861 | A | 12/1977 | Yukinaga et al. |
| 4,071,524 | A | 1/1978 | Banitt |
| 4,111,680 | A | 9/1978 | Yukinaga et al. |
| 4,111,683 | A | 9/1978 | Singer |
| 4,116,671 | A | 9/1978 | Yukinaga et al. |
| 4,173,637 | A | 11/1979 | Nishiyama et al. |
| 4,173,638 | A | 11/1979 | Nishiyama et al. |
| 4,183,854 | A | 1/1980 | Crossley |
| 4,212,981 | A | 7/1980 | Yukinaga et al. |
| 4,240,820 | A | 12/1980 | Dickore et al. |
| 4,279,639 | A | 7/1981 | Okamoto et al. |
| 4,405,644 | A | 9/1983 | Kabbe et al. |
| 4,410,697 | A | 10/1983 | Török et al. |
| 4,437,878 | A | 3/1984 | Acker et al. |
| 4,468,380 | A | 8/1984 | O'Doherty et al. |
| 4,473,579 | A | 9/1984 | Devries et al. |
| 4,511,571 | A | 4/1985 | Böger et al. |
| 4,514,571 | A | 4/1985 | Nakai et al. |
| 4,526,997 | A | 7/1985 | O'Doherty et al. |
| 4,623,662 | A | 11/1986 | DeVries et al. |
| 4,643,849 | A | 2/1987 | Hirai et al. |
| 4,740,520 | A | 4/1988 | Hallenbach et al. |
| 4,760,063 | A | 7/1988 | Hallenbach et al. |
| 4,808,588 | A | 2/1989 | King |

(Continued)

FOREIGN PATENT DOCUMENTS

| CN | 2 146 707 | 10/1995 |
| DE | 487 014 | 11/1929 |
| DE | 511 468 | 10/1930 |
| DE | 523 437 | 4/1931 |
| DE | 2436179 C2 | 2/1975 |
| DE | 25 01 648 A1 | 7/1975 |
| DE | 2436179 A1 | 10/1981 |
| DE | 3305866 A1 | 8/1984 |
| DE | 35 29 247 A1 | 2/1987 |
| DE | 35 40 377 A1 | 5/1987 |

(Continued)

OTHER PUBLICATIONS

The many faces of Carbon Dioxide , Oct. 2000, Katie Walter.*
Bickel, Pharmocology and Biochemistry of N-Oxides. (1996).*
Caplus 86:72448, Abstract JP 57053785, Pyridine derivatives, Maeda Ryozo et al., Nov. 15, 1982.
Caplus 84:180049, Abstract JP 56029871, Hamada Yoshinori et al., Jul. 10, 1981.
Caplus 84:43857, Abstract JP 58021626, Maeda Ryozo et al., May 2, 1983.
Abstract of JP 55162772, Substituted acetic derivatives, Shionogi & Co., May 23, 1980.

(Continued)

*Primary Examiner* — Rita Desai
(74) *Attorney, Agent, or Firm* — Millen, White, Zelano & Branigan, P.C.

(57) ABSTRACT

This invention relates to new aryl ureas and methods for their synthesis. The inventive compounds are useful in the treatment of (i) raf mediated diseases, for example, cancer, (ii) p38 mediated diseases such as inflammation and osteoporosis, and (iii) VEGF mediated diseases such as angiogenesis disorders.

39 Claims, No Drawings

U.S. PATENT DOCUMENTS

| | | | |
|---|---|---|---|
| 4,820,871 A | 4/1989 | Kissener et al. |
| 4,863,924 A | 9/1989 | Haga et al. |
| 4,973,675 A | 11/1990 | Israel et al. |
| 4,983,605 A | 1/1991 | Kondo et al. |
| 4,985,449 A | 1/1991 | Haga et al. |
| 5,036,072 A | 7/1991 | Nakajima et al. |
| 5,059,614 A | 10/1991 | Lepage et al. |
| 5,098,907 A | 3/1992 | Kondo et al. |
| 5,130,331 A | 7/1992 | Pascual |
| 5,162,360 A | 11/1992 | Creswell et al. |
| 5,185,358 A | 2/1993 | Creswell et al. |
| 5,312,820 A | 5/1994 | Ashton et al. |
| 5,319,099 A | 6/1994 | Kamata et al. |
| 5,399,566 A | 3/1995 | Katano et al. |
| 5,423,905 A | 6/1995 | Fringeli |
| 5,429,918 A | 7/1995 | Seto et al. |
| 5,447,957 A | 9/1995 | Adams et al. |
| 5,470,882 A | 11/1995 | Dixon et al. |
| 5,500,424 A | 3/1996 | Nagamine et al. |
| 5,508,288 A | 4/1996 | Forbes et al. |
| 5,596,001 A | 1/1997 | Hamanaka |
| 5,597,719 A | 1/1997 | Freed et al. |
| 5,696,138 A | 12/1997 | Olesen et al. |
| 5,698,581 A | 12/1997 | Kleemann et al. |
| 5,773,459 A | 6/1998 | Tang et al. |
| 5,780,483 A | 7/1998 | Widdowson et al. |
| 5,807,891 A | 9/1998 | Bold et al. |
| 5,814,646 A | 9/1998 | Heinz et al. |
| 5,886,044 A | 3/1999 | Widdowson et al. |
| 5,891,895 A | 4/1999 | Shiraishi et al. |
| 5,908,865 A | 6/1999 | Doi et al. |
| 5,929,250 A | 7/1999 | Widdowson et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,020,345 A | 2/2000 | Vacher et al. |
| 6,022,884 A | 2/2000 | Mantlo et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,133,319 A | 10/2000 | Widdowson |
| 6,143,764 A | 11/2000 | Kubo et al. |
| 6,147,116 A | 11/2000 | Barbachyn et al. |
| 6,150,415 A | 11/2000 | Hammock et al. |
| 6,174,901 B1 | 1/2001 | Mantlo et al. |
| 6,178,399 B1 | 1/2001 | Takebayashi et al. |
| 6,180,675 B1 | 1/2001 | Widdowson et al. |
| 6,187,799 B1 | 2/2001 | Wood et al. |
| 6,211,373 B1 | 4/2001 | Widdowson et al. |
| 6,218,539 B1 | 4/2001 | Widdowson |
| 6,242,601 B1 | 6/2001 | Breu et al. |
| 6,262,113 B1 | 7/2001 | Widdowson et al. |
| 6,271,261 B1 | 8/2001 | Widdowson |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,391,917 B1 | 5/2002 | Petrie et al. |
| 7,329,670 B1 | 2/2008 | Dumas et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2002/0042517 A1 | 4/2002 | Uday et al. |
| 2002/0062763 A1 | 5/2002 | Macholdt et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0128321 A1 | 9/2002 | Widdowson et al. |
| 2002/0137774 A1 | 9/2002 | Riedl et al. |
| 2002/0165394 A1 | 11/2002 | Dumas et al. |
| 2003/0144278 A1 | 7/2003 | Riedl et al. |

FOREIGN PATENT DOCUMENTS

| | | | |
|---|---|---|---|
| DE | 253997 A1 | | 2/1988 |
| EP | 0016371 A1 | | 10/1980 |
| EP | 0107214 A2 | | 9/1983 |
| EP | 0116932 A1 | | 8/1984 |
| EP | 0192263 B1 | | 8/1986 |
| EP | 0202538 A1 | | 11/1986 |
| EP | 0230400 A2 | | 7/1987 |
| EP | 0233559 B1 | | 8/1987 |
| EP | 0242666 A1 | | 10/1987 |
| EP | 0264904 A2 | | 4/1988 |
| EP | 0335156 A1 | | 10/1989 |
| EP | 0359148 A1 | | 3/1990 |
| EP | 0371876 A1 | | 6/1990 |
| EP | 0379915 A1 | | 8/1990 |
| EP | 0380048 A2 | | 8/1990 |
| EP | 0381987 A1 | | 8/1990 |
| EP | 0405233 A1 | | 1/1991 |
| EP | 0425443 A1 | | 5/1991 |
| EP | 04599887 | | 12/1991 |
| EP | 0676395 | | 10/1995 |
| EP | 0860433 A1 | | 8/1998 |
| FR | 1 457 172 | * | 9/1966 |
| GB | 828 231 | * | 10/1956 |
| GB | 771 333 | * | 3/1957 |
| GB | 921 682 | * | 3/1963 |
| GB | 1 590 870 | | 6/1981 |
| IR | 26555 | * | 7/2000 |
| JP | 44 2569 | * | 2/1944 |
| JP | 50-76072 | * | 6/1975 |
| JP | 50-77375 | * | 6/1975 |
| JP | 50-149668 | * | 11/1975 |
| JP | 51-63170 | * | 6/1976 |
| JP | 51-80862 | * | 7/1976 |
| JP | 53-86033 | * | 7/1978 |
| JP | 54-032468 | * | 9/1979 |
| JP | 55-98152 | * | 7/1980 |
| JP | 55-124763 | * | 9/1980 |
| JP | 55-162772 | | 12/1980 |
| JP | 3 532 47 | * | 3/1991 |
| JP | 08-301841 | | 11/1996 |
| JP | 10-306078 | | 11/1998 |
| LB | 6124 | * | 5/2000 |
| WO | 90/02112 | | 3/1990 |
| WO | 93/18028 | | 9/1993 |
| WO | 93/24458 | | 12/1993 |
| WO | 94/14801 | | 7/1994 |
| WO | 94/18170 | | 8/1994 |
| WO | 94/22807 | | 10/1994 |
| WO | 94/25012 | | 11/1994 |
| WO | 95/02591 | | 1/1995 |
| WO | 95/07922 | | 3/1995 |
| WO | 95/13067 | | 5/1995 |
| WO | 95/31451 | | 11/1995 |
| WO | 95/33458 | | 12/1995 |
| WO | 96/10559 | | 4/1996 |
| WO | 96/13632 | | 5/1996 |
| WO | 96/25157 | | 8/1996 |
| WO | 96/40673 | | 12/1996 |
| WO | 96/40675 | | 12/1996 |
| WO | 97/17329 | | 5/1997 |
| WO | 97/29743 | | 8/1997 |
| WO | 97/30992 | | 8/1997 |
| WO | 97/40028 | | 10/1997 |
| WO | 97/45400 | | 12/1997 |
| WO | 97/49399 | | 12/1997 |
| WO | 97/49400 | | 12/1997 |
| WO | 98/17267 | | 4/1998 |
| WO | 98/22103 | | 5/1998 |
| WO | 98/22432 | | 5/1998 |
| WO | 98/52558 | | 11/1998 |
| WO | 98/52559 | | 11/1998 |
| WO | 99/00357 | | 1/1999 |
| WO | 99/00370 | | 1/1999 |
| WO | 99/20617 | | 4/1999 |
| WO | 99/21835 | | 5/1999 |
| WO | 99/23091 | | 5/1999 |
| WO | 99/24398 | | 5/1999 |
| WO | 99/32106 | | 7/1999 |

| WO | 99/32110 | 7/1999 |
| WO | 99/32111 | 7/1999 |
| WO | 99/32436 | 7/1999 |
| WO | 99/32437 | 7/1999 |
| WO | 99/32455 | 7/1999 |
| WO | 99/32463 | 7/1999 |
| WO | 99/33458 | 7/1999 |
| WO | 00/17175 | 3/2000 |
| WO | 00/41698 | 7/2000 |
| WO | 00/42012 | 7/2000 |
| WO | 00/43366 | 7/2000 |
| WO | 00/43384 | 7/2000 |
| WO | 00/47577 | 8/2000 |
| WO | 00/55139 | 9/2000 |
| WO | 00/55152 | 9/2000 |
| WO | 00/56331 | 9/2000 |
| WO | 01/36403 A1 | 5/2001 |
| WO | 02/24635 A2 | 3/2002 |
| WO | WO 02/062763 A2 | 8/2002 |
| WO | WO 03/047579 A1 | 6/2003 |
| WO | WO 03/068223 A1 | 8/2003 |
| WO | WO 03/068228 A1 | 8/2003 |
| WO | WO 03/068229 A1 | 8/2003 |
| WO | WO 2004/078128 A2 | 9/2004 |
| WO | WO 2004/078746 A2 | 9/2004 |
| WO | WO 2004/078747 A1 | 9/2004 |
| WO | WO 2004/078748 A2 | 9/2004 |
| WO | WO 2004/113274 A2 | 12/2004 |
| WO | WO 2005/000284 A2 | 1/2005 |
| WO | WO 2005/009961 A2 | 2/2005 |

OTHER PUBLICATIONS

Abstract of EP 0 202 538 A1, "Growth Promoting Agents", Nov. 26, 1986.
Abstract of DE 3305866 A (EP equivalent 116,932), R.D. Acker at al., Aug. 23, 1984.
Abstract of EP 116,932, Aug. 29, 1984.
Abstract of EP 16,371, Oct. 1, 1980.
Abstract of EP 0 676 395 (U.S. equivalent 5,698,581), Dec. 16, 1997.
Abstract WO 9822103, Hedge May 28, 1998, Philip et al.
Chemical Abstract, vol. 116, No. 21, May 25, 1992, pp. 741-742.
Tarzia, G. et al., Synthesis and anit-inflammatory properties of some pyrrolo(1H,3H) [3,4-d]pyrimidin-2-ones and pyrrolo(1H,6H)[3,4-d]pyrimidin-2-ones. Chemical Abstracts, vol. 91, 1979, p. 594.
White, A. D., et al., "Heterocyclic Ureas: Inhibitors of Acyl-CoA:Cholesterol O-Acyltransferase as Hypochelesterolemic Agents", J. Med. Chem. 1996, 39, pp. 4382-4395.
Audia, James E., et al., "Potent Selective Tetrahydro-β-carboline Antagonists of the Serotonin 2B (5HT$_{2B}$) Contractile Receptor in the Rat Stomach Fundus" J. Med. Chem. 1996, 39, pp. 2773-2780.
Forbes, Ian T., "N-(1-Methyl-5-indolyl)-N-(3-methyl-5-isothiazolyl)urea: A Novel, High-Affinity 5-HT$_{2B}$ Receptor Antagonist", Journal of Medicinal Chem. vol. 38, No. 6, Mar. 17, 1995, pp. 855-857.
Boulton, A. J., et al., "Heterocyclic Rearrangements. Part X.[1] A Generalised Monocyclic Rearrangement", J. Chem. Soc. (C), 1967, pp. 2005-2007.
W. Kolch, et al., "Raf-1 protein kinase is required for growth of induced NIH/3T3 cells", Letters to Nature, vol. 349, Jan. 31, 1991, pp. 426-428.
M. Fridman, et al., "The Minimal Fragments of c-Raf-1 and NF1 That Can Suppress v-Ha-Ras-Induced Malignant Phenotype", The Journal of Biological Chemistry, vol. 269, No. 48, Dec. 2, 1994, pp. 30105-30108.
G. L. Bolton, et al., Chapter 17. Ras Oncogene Directed Approaches in Cancer Chemotherapy, Annual Reports in Medicinal Chemistry, vol. 29, 1994, pp. 165-174.
J. L. Bos "ras Oncogenes in Human Cancer: A Review", Cancer Research, vol. 49, Sep. 1, 1989, pp. 4682-4689.
Michaelis, Justus, Liebigs Ann. Chem. (JLACBF) 397, 1913, 143.
B. P. Monja, et al., "Antitumor activity of a phosphorothioate antisense oligodeoxynucleotide targeted against C-raf kinase", Nature Medicine, vol. 2, No. 6, Jun. 1996, pp. 668-675.

Lee, et al., Bicyclic Imidazoles as a Novel Class of Cytokine Biosynthesis Inhibitors, Annuals N.Y. Academy of Science, 1993, pp. 149-170.
F. Lepage, et al., "New N-aryl isoxazolecarboxamides and N-isoxazolybenzamides as anticonvulsant agents", Eur. J. Med. Chem, vol. 27, 1992, pp. 581-593.
Ridley, et al., "Actions of IL-1 are Selectively Controlled by p38 Mitogen-Activated Protein Kinase", The American Association of Immunologists, 1997, p. 3165-73.
N. S. Magnuson, et al., "The Raf-1 serine/threonine protein kinase", Cancer Biology, vol. 5, 1994, pp. 247-253.
G. Daum, et al., "The ins and outs of Raf Kinases", TIBS 19, Nov. 1994, pp. 474-480.
Grant, A.M. et al.: "Hypotensive thiadiazoles", J. Med. Chem. (1972), 15(10), p. 1082-4.
Russo, F. et al. "Synthesis of 2,6-substituted derivatives of 5H-1,3,4-thiadiazolo=3,2-al-s triazine-5,7-dione" Farmaco, Ed.Sci. (1978), 33(12), 972-83.
Joseph T. Bruder et al., Journal of Virology, Jan. 1997, "Adenovirus Infection Stimulates the Raf/MAPK Signaling Pathway and Induces Interleukin-8 Expression", May 17, 1996, pp. 398-404.
Foussard-Blanpin, Odetter: "Comparative pharmacodynamic study of variously substituted carboxamides of the central nervous system" Ann. Pharm. Fr. (1982), 40 (4), pp. 339-350.
Kubo, Hiroshi et al., vol. 18, No. 1, Jan.-Feb. 1970 "Herbicidal activity of 1,3,4-thiadiazole derivatives" J. Agr. Food Chem. (1970), 18(1), pp. 60-65.
Avruch et al., "Raf meets Ras: completing the framework of a signal transduction pathway", TIBS 19; Jul. 1994; pp. 279-281.
Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.
Caplus 113:142130, Abstract of JP 2023337, Silver halide photographic material containing phenolic cyan coupler a colorless cyan coupler, Toshihiko Yagl at al., Jan. 25, 1990.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat", Chemical Life Science, pp. 157-166, 1977.
Caplus 127:293717, "Optical properties of segmented oligourethane with azomethine terminal fragments", National Academy of Science of Ukraine, M. V. Kurik et al., pp. 2038-2041, 1996.
Caplus 127:273945, "Quantitative structure-biodegradability studies: an investigation of the MITI aromatic compound database", School of Pharmacy and Chemistry, J. C. Dearden, Biodegradability Prediction Edited by Willie J.G.M. Peijnenburg et al., NATO ASI Series, 2. Environment—vol. 23, pp. 93-104, 1996.
Caplus 126:166148, "Inhibitors of coenzyme A-independent transacylase induce apoptosis in human HL-60 cells", James D. Winkler et al., J. Pharmacol. Exp. Ther. pp. 956-968, 1996.
Caplus 98:78152, Abstract of JP 57185219, "Antitumor benzophenone derivatives", Nov. 15, 1982.
Caplus 72:79046, Abstract of CH 479557, "Tuberculostatic and cancerostatic polybasic ureas", Dr. A. Wander, Oct. 15, 1969.
Caplus 125:245169, "Production of murine monoclonal antibodies against sulcofuron and flucofuron by in vitro immunization", G. A. Bonwick et al., J. Immunol. Methods, pp. 163-173, 1996.
Caplus 127:34137f, "Preparation of quinoline an dquinazoline derivatives inhibiting platelet-derived growth factor receptor autophosphorylation", Kazuo Kubo et al., May 15, 1997.
Caplus 131:58658k, "Inhibition of raf kinase using symmetrical and unsymmetrical substituted diphenyl ureas", Miller, Scott, Jul. 1, 1999.
Caplus 131:87909y, "Inhibition of p38 kinase activity using substituted heterocyclic ureas", Jacques Dumas, Jul. 1, 1999.
Caplus 131:73649b, "Preparation of pyrazolyl aryl ureas and related compounds as p38kinase inhibitor", Jacques Dumas, Jul. 1, 1999.
Joseph V. Simone, "Cecil Textbook of Medicine", 20th Edition, vol. 1, Feb. 3, 1997. pp. 1004-1010.
Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.

Jacqueline E. van Muijlwijk-Koezen at al., "Isoquinoline and Quinazoline Urea Analogues as Antagonists for the Human Adenosine $A_3$ Receptor", J. Ed. Chem. 2000, 43, pp. 2227-2238, Jan. 3, 2000.

Jacques Dumas et al., "1-Phenyl-5-pyrazolyl Ureas: Potent and Selective p38 Kinase Inhibitors", Bioorganic & Medicinal Chemistry Letters, pp. 2051-2054, May 2, 2000.

Robert W. Caning et al., "1-(3-Cyanobenxylpiperidin-4-yl)-5-methyl-4-phenyl-1,3-dihydroimidazol-2-one: A Selective High-Affinity Antagonist for the Human Dopamine $D_4$ Receptor with Excellent Selectivity over Ion Channels", J. Med. Chem., 1999, 42, pp. 2706-2715.

Abstract WO 9822103, May 28, 1998, John Philip Hedge et al.

Abstract of DE 3305866A1, Aug. 29, 1984, Dr. Acker Rolf-Dieter et al.

Abstract of EP 4931(equivalent 4,240,820), K. Dickore e tal. (1980).

Dumas, J.. "CAS Substructure," May 6, 1997, pp. 1-29.

Scott,Bill, "Substructure (Patent Families)", Aug. 11, 1997, pp. 1-19.

Scott, Bill, "Substructure #2", Nov. 25, 1997, pp. 1-3.

"Beilstein number" Collection, 28 pages (1997).

"Beilstein Collection", 4 pages (1997).

Scott, Bill, "Substructure Search", Dec. 2, 1997, pp. 1-51.

Substructure Search, pp. 1-30. (1997).

*Derwent World Patents Index Search*, pp. 20-26. (1997).

Abstract of EP 116,932 (1984).

Abstract of EP 676,395 (1995).

Abstract of EP 0 202 538 (1986).

Abstract of EP 16,371 (1980).

Co-pending U.S. Appl. No. 10/361,844, filed Feb. 11, 2003.

Co-pending U.S. Appl. No. 10/361,850, filed Feb. 11, 2003.

Co-pending U.S. Appl. No. 10/060,396, filed Feb. 1, 2002.

Co-pending U.S. Appl. No. 09/458,014, filed Dec. 10, 1999.

Co-pending U.S. Appl. No. 10/125,369, filed Apr. 19, 2002.

Co-pending U.S. Appl. No. 09/889,227, filed Jul. 12, 2001.

XP-001145779 "Antitumor Activity of a C-raf Antisense Oligonucleotide in Combination with Standard Chemotherapeutic Agents against Various Human Tumors Transplanted Subcutaneously into Nude Mice", Thomas Geiger et al., vol. 3, 1179-1185, Jul. 1997.

XP-002232130, "A Phase I Trial of H-ras Antisense Oligonucleotide ISIS 2503 Administered as a Continuous Intravenous Infusion in Patients with Advanced Carcinoma", C. Casey Cunningham et al., 2001 American Cancer Society, vol. 92, No. 5, pp. 1265-1271.

Abstract of EP 4931A (Equivalent 4,240,820), Dickore, K. et al., Oct. 31, 1979.*

Abstract of EP 0405233A1, Tetsuo Sekiya et al., Jun. 15, 1989.*

XP-001145518 # 4956 Potent *Raf* Kinase Inhibitors from the Diphenylurea Class: Structure Activity Relationships, B. Riedl et al., Bayer Corporation (Mar. 2001).

XP-001145481 +2921 Phase I and Pharmacokinetic Study of the Raf Kinase Inhibitor Bay 43-9006 in Patients with Locally Advanced or Metastic Cancer, Dirk Strumberg et al.Bayer AG (Mar. 2001).

XP-002233466, MEDLINE/NLM, NLM8336809—[Intra-arterial ACNU, CDDP chemotherapy for brain metastases from lung cancer: comparison of cases with and without intra-arterial mannitol infusion], Iwadate Y et al. (Jun. 1993).

Wilhelm, Scott et al., BAY43-9006 Exhibits Broad Spectrum Oral Antitumor Activity and Targets the RAF/MEK/ERK Pathway and Receptor Tyrosine Kinases Involved in Tumor Progression and Angiogenesis, Cancer Research 64, 7099-7109, Oct. 1, 2004.

Siu, L et al., Phase I study of oral raf-1 kinase inhibitor BAY 43-9006 with gemcitabine in patients with advanced solid tumors, 2003 39th ASCO Annual Meeting, Proc. Am. Soc. Clin. Oncol. 22, p. 207, 2003 (Abstr 828).

Mross, K. et al., Drug-drug interaction pharmacokinetic study with the Raf kinase inhibitor (RKI) BAY 43-9006 administered in combination with irinotecan (CPT-11) in patients with solid tumors, International Journal of Clinical Pharmacology and Therapeutics, vol. 41—No. Dec. 2003 (618-619).

Wan, Paul T.C. et al., Mechanism of Activation of the RAF-ERK Signaling Pathway by Oncogenic Mutations of B-RAF, Cell, vol. 116, (Mar. 19, 2004), 855-867.

Khire, Uday et al., Omega-carboxypyridyl substituted ureas as Raf kinase inhibitors: SAR of the amide substituent, Bioorganic & Medicinal Chemistry Letters, 14 (2004), 783-786.

Bankston, Donald et al., A Scaleable Synthesis of BAY-43-9006: A Potent Raf Kinase Inhibitor for the Treatment of Cancer, Organic Process Research & Development, 2002, 6, 777-781.

Dumas, Jacques et al., Synthesis and Pharmacological Characterization of a Potent, Orally Active p38 Kinase Inhibitor, Bioorganic & Medicinal Chemistry Letter, 12 (2002) 1559-1562.

Redman, Aniko M. et al., p38 Kinase Inhibitors for the Treatment of Arthritis and Osteoporosis: Thienyl, Furyl, and Pyrrolyl Ureas, Bioorganic & Medicinal Chemistry Letters, 11 (2001) 9-12.

Dumas, Jacques et al., Discovery of a New Class of p38 Kinase Inhibitors, Bioorganic & Medicinal Chemistry Letters, 10 (2000) 2047-2050.

Sorbera et al., Bay-43-9006 Oncolytic Raf Kinase Inhibitor, Drugs of the Future 2002, 27(12): 1141-1147.

Dumas, Jacques, Protein Kinase Inhibitors from the Urea Class, Current Opinion in Drug Discovery & Development, 2002, 5(5): 718-727.

Richly, H. et al., A phase I clinical and pharmacokinetic study of Raf kinase inhibitor (RKI) BAY-43-9006 administered in combination with doxorubicin in patients with solid tumors, International Journal of Clinical Pharmacology and Therapeutics, vol. 41—No. Dec. 2003 (620-621).

Dumas, J., Protein Kinase Inhibitors from the Urea Class, Curr. Opin. Drug. Discov. Dev., 2002, 5(5), 718-727 (Abstract).

Dumas, J. et al., Recent Developments in the Discovery of Protein Kinase Inhibitors from the Urea Class, Curr. Opin. Drug Discov. Dev., 2004, 7(5), 600-616, (Abstract).

DeGrendele, H., Activity of the Raf Kinase Inhibitor BAY-43-9006 in Patients with Advanced Solid Tumors, Clin. Colorectal Cancer 2003, 3(1), 16-18, (Abstract).

Sorbera, L.A. et al., Oncolytic Raf Kinase Inhibitor, Drugs of the Future 2002, 27(12), 1141-1147 (Abstract).

DeGrendele, H., Activity of the Raf Kinase Inhibitor BAY-43-9006 in Patients with Advanced Solid Tumors, Clin. Colorectal Cancer May 2003, 3(1), 16-18.

MRC-01272 Anti-Tumor Efficacy of Major Metabolic of BAY-43-9006; C. Carter et al. ; Aug. 4, 2004.

Abstract of EP 4931 A (Equivalent 4,240,820), Bayer AG, 1 page Oct. 24, 1979.

Abstract of EP 0405233A1, Tetsuo Sekiya et al., 1 page Oct. 27, 1993.

A "Notice of References Cited" from the USPTO for U.S. Appl. No. 08/995,749, filed Dec. 22, 1997, Inhibition of P38 Kinase Using Symmetrical and Unsymmetrical Diphenyl Ureas, 2 pages.

A "Notice of References Cited" from the USPTO for U.S. Appl. No. 09/083,399, filed May 22, 1998, Patent 6187799 issued Feb. 13, 2001, Inhibition of Raf Kinase Activity Using Aryl Ureas, 1 page.

A "Notice of References Cited" from the USPTO for U.S. Appl. No. 09/425,228, filed Oct. 22, 1999, Omega-Carboxyaryl Substituted Diphenyl Ureas As Raf Kinase Inhibitors, 3 pages.

A "Notice of References Cited" from the USPTO for U.S. Appl. No. 09/425,229, filed Oct. 22, 1999, Omega-Carboxy Aryl Substituted Diphenyl Ureas As p38 Kinase Inhibitors, 1 page.

A "Notice of References Cited" from the USPTO for U.S. Appl. No. 09/458,015, filed Dec. 10, 1999, Inhibition Of p38 Kinase Using Symmetrical And Unsymmetrical Diphenyl Ureas, 1 page.

A "Notice of References Cited" from the USPTO for U.S. Appl. No. 09/472,232, filed Dec. 27, 1999, Patent 7329670 issued Feb. 12, 2008, Inhibition of Raf Kinase Using Aryl and Heteroaryl Substituted Heterocyclic Ureas, 1 page.

A "Notice of References Cited" from the USPTO for U.S. Appl. No. 09/773,604, filed Feb. 2, 2001, Publication No. US 2001-0034447-A1, Publication Date Oct. 25, 2001, Omega-carboxyaryl Substituted Diphenyl Ureas as Raf Kinase Inhibitors, 1 page.

A "Notice of References Cited" from the USPTO for U.S. Appl. No. 09/773,659, filed Feb. 2, 2001, Publication No. US 2001-0011135-A1, Publication Date: Aug. 2, 2001, Omega-carboxyaryl Substituted Diphenyl Ureas As Raf Kinase Inhibitors, 1 page.

A "Notice of References Cited" from the USPTO for U.S. Appl. No. 09/773,672, filed Feb. 2, 2001, Publication No. US 2001-0016659-

A1, Publication Date: Aug. 23, 2001, Omega-carboxyaryl substituted Diphenyl Ureas as Raf Kinase Inhibitors, 1 page.
A "Notice of References Cited" from the USPTO for U.S. Appl. No. 09/773,675, filed Feb. 2, 2001, Publication No. US 2001-0011136-A1 , Publication Date: Aug. 2, 2001, Omega-Carboxyaryl Substituted Diphenyl Ureas as Raf Kinase Inhibitors, 1 page.
A "Notice of References Cited" from the USPTO for U.S. Appl. No. 09/776,935 filed Dec. 22, 1998, Inhibition Of p38 Kinase Using Aryl And Heteroaryl Substituted Heterocyclic Ureas, 1 page.
A "Notice of References Cited" from the USPTO for U.S. Appl. No. 09/776,936, filed Dec. 22, 1998, Inhibition Of Raf Kinase Using Symmetrical and Unsymmetrical Substituted Diphenyl Ureas, 1 page.
A "Notice of References Cited" from the USPTO for U.S. Appl. No. 09/777,920, filed Feb. 7, 2001, Inhibition of RAF kinase using quinolyl, isoquinolyl or pyridyl ureas, 1 page.
A "Notice of References Cited" from the USPTO for U.S. Appl. No. 09/948,915, filed Sep. 10, 2001, Omega-Carboxyaryl Substituted Diphenyl Ureas As Raf Kinase Inhibitors, 1 page.
A "Notice of References Cited" from the USPTO for U.S. Appl. No. 10/042,226, filed Jan. 11, 2002, Omega-Carboxyaryl Substituted Diphenyl Ureas As Raf Kinase Inhibitors, 1 page.
Abandoned U.S. Appl. No. 09/776,935 filed Dec. 22, 1998, Dumas et al.
Co-pending U.S. Appl. No. 09/776,936 filed Dec. 22, 1998, Miller et al.
Co-pending U.S. Appl. No. 09/993,647 filed Nov. 27, 2001, Riedl et al., published as 2003-0181442, Sep. 25, 2003.
Co-pending U.S. Appl. No. 10/071,248 filed Feb. 11, 2002, Riedl et al.
Co-pending U.S. Appl. No. 10/086,417 filed Mar. 4, 2002, Riedl et al.
Co-pending U.S. Appl. No. 10/308,187 filed Dec. 3, 2002, Carter et al.
International search report for International Application No. PCT/US98/10375 dated Sep. 3, 1998, Inhibition Of p38 Kinase Activity by Aryl Ureas, publication No. 98/52558, publication date Nov. 26, 1998, 1 page.
International search report for International Application No. PCT/US98/10376 dated Jul. 30 ,1998, Raf Kinase Inhibitors, publication No. WO 98/52559, publication date Nov. 26, 1998, 1 page.
International search report for International Application No. PCT/US98/26078 dated Apr. 2, 1999, Inhibition Of Raf Kinase Using Substituted Heterocyclic Ureas, publication No. WO 99/32106, publication date Jul. 1, 1999, 2 pages.
International search report for International Application No. PCT/US98/26079 dated Apr. 12, 1999, Inhibition Of p38 Kinase Activity Using Aryl And Heteroaryl Substituted Heterocyclic Ureas, publication No. WO 99/32110, publication date Jul. 1, 1999, 1 page.
International search report for International Application No. PCT/US98/26080 dated Apr. 12, 1999, Inhibition Of p38 Kinase Using Substituted Heterocyclic Ureas, publication No. WO 99/32111, publication date Jul. 1, 1999, 1 page.

International search report for International Application No. PCT/US98/26081 dated Apr. 2, 1999, Inhibition of Raf Kinase Using Symmetrical and Unsymmetrical Substituted Diphenyl Ureas, publication No. WO 99/32436, publication date Jul. 1, 1999, 1 page.
International search report for International Application No. PCT/US98/26082 dated May 12, 1999, Inhibition of Raf Kinase Using Aryl and Heteroaryl Substituted Heterocyclic Ureas, publication No. WO 99/32455, publication date Jul. 1, 1999, 1 page.
International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.
International search report for International Application No. PCT/US00/00648 dated Jun. 29, 2000, Omega-Carboxyaryl Substituted Diphenyl Ureas as RAF Kinase Inhibitors, publication No. WO 00/42012 A1, publication date Jul. 20, 2000, 2 pages.
International search report for International Application No. PCT/US00/00768 dated May 16, 2000, Omega-Carboxy Aryl Substituted Diphenyl Ureas As p38 Kinase Inhibitors, publication No. WO 00/41698 Al, publication date Jul. 20, 2000, 1 page.
International search report for International Application No. PCT/US02/12064 dated Sep. 20, 2002, Heteroaryl Ureas Containing Nitrogen Hetero-Atoms As p38 Kinase Inhibitors, publication No. 02/085859, publication date Oct. 31, 2002, 2 pages.
International search report for International Application No. PCT/US02/12066 dated Sep. 27, 2002, Inhibition Of Raf Kinase Quinolyl, Isoquinolyl or Pyridyl Ureas, publication No. 02/085857, publication date Oct. 31, 2002, 2 pages.
Supplemental search report from the EPO for European application EP 98963809.3 dated Mar. 30, 2001, Inhibition Of Raf Kinase Using Symmetrical and Unsymmetrical Substituted Diphenyl Ureas, publication No. 1049664, publication date Jul. 1, 1999, granted Mar. 16, 2005, 4 pages.
Supplemental search report from the EPO for European application EP 98963810.1 dated Dec. 21, 2000, Inhibition Of Raf Kinase Using Aryl and Heteroaryl Substituted Heterocyclic Ureas, publication No. 1056725, publication date Jul. 1, 1999, granted Jun. 7, 2006, 4 pages.
Supplemental search report from the EPO for European application EP 98965981.8 dated Dec. 21, 2000, Inhibition Of Raf Kinase Using Substituted Heterocyclic Ureas, publication No. 1047418, publication date Jul. 1, 1999, granted Jul. 27, 2005, 8 pages.
Supplemental search report from the EPO for European application EP 00903239.2 dated Aug. 7, 2002, Omega-Carboxyaryl Substituted Diphenyl Ureas As Raf Kinase Inhibitors, publication No. EP 1140840, published Jul. 20, 2000, granted Mar. 22, 2006, 6 pages.
Abandoned U.S. Appl. No. 09/640,780 filed Aug. 18, 2000, Dumas et al.

* cited by examiner

ARYL UREAS AS KINASE INHIBITORS

This application claims priority to provisional application Ser. No. 60/354,937, filed Feb. 11, 2002.

FIELD OF THE INVENTION

This invention relates to aryl ureas and methods for their synthesis. The inventive compounds are useful in the treatment of
(i) raf mediated diseases, for example, cancer,
(ii) p38 mediated diseases such as inflammation and osteoporosis, and
(iii) VEGF mediated diseases such as angiogenesis disorders.

BACKGROUND OF THE INVENTION

Activation of the Ras signal transduction pathway indicates a cascade of events that have a profound impact on cellular proliferation, differentiation, and transformation. Raf kinase, a downstream effector of Ras, is a key mediator of these signals from cell surface receptors to the cell nucleus (Lowy, D. R.; Willumsen, B. M. *Ann. Rev. Biochem.* 1993, 62, 851; Bos, J. L. *Cancer Res.* 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75). Thus, small molecule inhibitors of Raf kinase activity are important agents for the treatment of cancer (Naumann, U.; Eisenmann-Tappe, I.; Rapp, U. R. *Recent Results Cancer Res.* 1997, 143, 237; Monia, B. P.; Johnston, J. F.; Geiger, T.; Muller, M.; Fabbro, D. *Nature Medicine* 1996, 2, 668).

Inhibition of p38 has been shown to inhibit both cytokine production (eg., TNFα, IL-1, IL-6, IL-8) and proteolytic enzyme production (eg., MMP-1, MMP-3) in vitro and/or in vivo. The mitogen activated protein (MAP) kinase p38 is involved in IL-1 and TNF signaling pathways (Lee, J. C.; Laydon, J. T.; McDonnell, P. C.; Gallagher, T. F.; Kumar, S.; Green, D.; McNulty, D.; Blumenthal, M. J.; Heys, J. R.; Landvatter, S. W.; Stricker, J. E.; McLaughlin, M. M.; Siemens, I. R.; Fisher, S. M.; Livi, G. P.; White, J. R.; Adams, J. L.; Yound, P. R. *Nature* 1994, 372, 739).

Clinical studies have linked TNFα production and/or signaling to a number of diseases including rheumatoid arthritis (Maini. *J. Royal Coll. Physicians London* 1996, 30, 344). In addition, excessive levels of TNFα have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoperosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taveme et al. *Parasitol. Today* 1996, 12, 290) including Plasmodium falciparum malaria (Perlmann et al. *Infect. Immunit.* 1997, 65, 116) and cerebral malaria (Rudin et al. *Am. J. Pathol.* 1997, 150, 257), non-insulin-dependent diabetes mellitus (NIDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). TNFα levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNFα has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al. *J. Invest. Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of TNFα production and MMP production, inhibition of mitogen activated protein (MAP) kinase p38 enzyme provides an approach to the treatment of the above listed diseases including osteoporosis and inflammatory disorders such as rheumatoid arthritis and COPD (Badger, A. M.; Bradbeer, J. N.; Votta, B.; Lee, J. C.; Adams, J. L.; Griswold, D. E. *J. Pharm. Exper. Ther.* 1996, 279, 1453).

Vasculogenesis involves the de novo formation of blood vessels from endothelial cell precursors or angioblasts. The first vascular structures in the embryo are formed by vasculogenesis. Angiogenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are highly specific for vascular endothelial cells (for reviews, see: Farrara et al. *Endocr. Rev.* 1992, 13, 18; Neufield et al. *FASEB J.* 1999, 13, 9). VEGF expression is induced by hypoxia (Shweiki et al. *Nature* 1992, 359, 843), as well as by a variety of cytokines and growth factors, such as interleukin-1, interleukin-6, epidermal growth factor and transforming growth factor.

To date, VEGF and the VEGF family members have been reported to bind to one or more of three transmembrane receptor tyrosine kinases (Mustonen et al. *J. Cell Biol.,* 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1-2 mm. Oxygen and nutrients may be supplied to cells in tumor smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.,* 1995, 92, 768). In addition, VEGF production in tumor regions where there is no angiogenesis may proceed through the ras signal transduction pathway (Grugel et al. *J. Biol. Chem.,* 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 143I, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859)

and several intracranial tumors (Plate et al. *Nature* 1992, 359, 845; Phillips et al. *Int. J. Oncol.* 1993, 2, 913; Berkman et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ.* 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opththalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels are low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR leads to inhibition of VEGF-mediated angiogenesis and permeabilization, KDR inhibitors will be useful in treatment of diseases characterized by abnormal angiogenesis and/or hyperpermeability processes, including the above listed diseases.

SUMMARY OF THE INVENTION

The invention relates to a compound of formula (I)

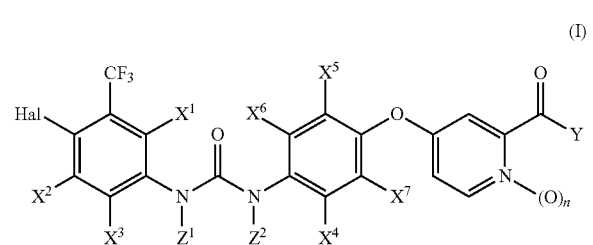

wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$Z^1$ and $Z^2$ are each H or OH, wherein only one of $Z^1$ or $Z^2$ can be OH.
$X^1$ to $X^7$ are each, independently, H, OH or $O(CO)C_1$-$C_4$ alkyl, and
n is 0 or 1,
with the proviso that at least one of conditions a-c is met,
 a) $Z^1$ or $Z^2$ is OH,
 b) $R^2$ is OH,
 c) n is 1,
or a salt thereof, e.g., a pharmaceutically acceptable salt thereof, or an isolated stereoisomer thereof (collectively referred to hereinafter as the compounds of the invention).

The term stereoisomer is understood to encompass diastereoisomers, enantiomers, geometric isomers, etc.

One of ordinary skill in the art will recognize that some of the compounds of Formula (I) can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures. All of these compounds, including cis isomers, trans isomers, diastereomic mixtures, racemates, nonracemic mixtures of enantiomers, substantially pure, and pure enantiomers, are considered to be within the scope of the present invention. Herein, substantially pure enantiomers is intended to mean that no more than 5% w/w of the corresponding opposite enantiomer is present.

The optical isomers can be obtained by resolution of the racemic mixtures according to conventional processes, for example, by the formation of diastereoisomeric salts using an optically active acid or base. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical chemical differences by methods known to those skilled in the art, for example, by chromatography or fractional crystallization. The optically active bases or acids are liberated from the separated diastereomeric salts. A different process for separation of optical isomers involves the use of a chiral chromatography column (e.g., chiral HPLC columns) optimally chosen to maximize the separation of the enantiomers. Suitable chiral HPLC columns are manufactured by Diacel, e.g., Chiracel OD and Chiracel OJ. The optically active compounds of Formula (I) can likewise be obtained by utilizing optically active starting materials.

The invention also comprises analogs of the compounds of the invention.

Preference is given to compounds of the invention when n is 1. These compounds particularly include compounds of the invention wherein n is 1 in formula (I), Y is $NHR^2$ and $R^2$ is H or $CH_3$, compounds of the invention wherein n is 1 in formula (I) and $X^1$ to $X^7$ are each H, compounds of the invention wherein n is 1 in formula (I) and $Z^1$ and $Z^2$ are each H, compounds of the invention wherein n is 1 in formula (I) and $Z^1$ is H and $Z^2$ is OH or $Z^1$ is OH and $Z^2$ is H, compounds of the invention wherein n is 1 in formula (I) and at least one of $X^1$ to $X^7$ is OH or $O(CO)C_1$-$C_4$ alkyl, compounds of the invention wherein n is 1 in formula (I), Y is $NHR^2$ and $R^2$ is $CH_2OH$, compounds of the invention wherein n is 1 in formula (I), Y is $NHR^2$ and $R^2$ is OH, and compounds of the invention wherein n is 1 in formula (I) and Y is OH.

Other compounds of the invention of interest are those wherein in formula (I) $Z^1$ is H and $Z^2$ is OH or $Z^1$ is OH and $Z^2$ is H. These particularly include compounds of the invention wherein in formula (I) $Z^1$ is H and $Z^2$ is OH or $Z^1$ is OH and $Z^2$ is H, and n is 0, compounds of the invention wherein in formula (I) $Z^1$ is H and $Z^2$ is OH or $Z^1$ is OH and $Z^2$ is H, n is 0, Y is $NHR^2$ and $R^2$ is H or $CH_3$, compounds of the invention wherein in formula (I) $Z^1$ is H and $Z^2$ is OH or $Z^1$ is OH and $Z^2$ is H, and n is 0 and $X^1$ to $X^7$ are each H, compounds of the invention wherein in formula (I) $Z^1$ is H and $Z^2$ is OH or $Z^1$ is OH and $Z^2$ is H, and n is 0 and at least one of $X^1$ to $X^7$ is OH or $O(CO)C_1$-$C_4$ alkyl, compounds of the invention wherein in formula (I) $Z^1$ is H and $Z^2$ is OH or $Z^1$ is OH and $Z^2$ is H, n is 0, Y is $NHR^2$ and $R^2$ is $CH_2OH$, compounds of the invention wherein in formula (I) $Z^1$ is H and $Z^2$ is OH or $Z^1$ is OH and $Z^2$ is H, n is 0, Y is $NHR^2$ and $R^2$ is OH, and compounds of the invention wherein in formula (I) $Z^1$ is H and $Z^2$ is OH or $Z^1$ is OH and $Z^2$ is H, and n is 0 and Y is OH.

Further compounds of the invention of interest are those wherein in formula (I), Y is $NHR^2$ and $R^2$ is OH. These compounds particularly include compounds of the invention wherein in formula (I), Y is $NHR^2$ and $R^2$ is OH and n is 0, compounds of the invention wherein in formula (I), Y is $NHR^2$ and $R^2$ is OH and n is 0 and $X^1$ to $X^7$ are each H, compounds of the invention wherein in formula (I), Y is $NHR^2$ and $R^2$ is OH and n is 0 and $Z^1$ and $Z^2$ are each H, compounds of the invention wherein in formula (I), Y is $NHR^2$ and $R^2$ is OH and n is 0 and $Z^1$ is H and $Z^2$ is OH or $Z^1$ is OH and $Z^2$ is H, and compounds of the invention wherein in formula (I), Y is $NHR^2$ and $R^2$ is OH and n is 0 and at least one of $X^1$ to $X^7$ is OH or $O(CO)C_1$-$C_4$ alkyl.

Compounds of the invention of interest are also those wherein in formula (I) Y is OH. These compounds particularly include compounds of the invention wherein in formula (I) Y is OH and n is 0, compounds of the invention wherein in formula (I) Y is OH and n is 0 and $X^1$ to $X^7$ are each H, compounds of the invention wherein in formula (I) Y is OH and n is 0 and $Z^1$ and $Z^2$ are each H, compounds of the invention wherein in formula (I) Y is OH and n is 0 and $Z^1$ is H and $Z^2$ is OH or $Z^1$ is OH and $Z^2$ is H, and compounds of the invention wherein in formula (I) Y is OH and n is 0 and at least one of $X^1$ to $X^7$ is OH or $O(CO)C_1$-$C_4$ alkyl.

Particularly preferred compounds include:
4-{4-[({[4-chloro-3-(trifluoromethyl)phenyl]amino}carbonyl)amino]phenoxy}-N-methyl-2-pyridine carboxamide 1-oxide.
4-{4-[({[4-bromo-3-(trifluoromethyl)phenyl]amino}carbonyl)amino]phenoxy}-N-methyl-2-pyridine carboxamide 1-oxide.
4-{4-[({[4-chloro-3-(trifluoromethyl)phenyl]amino}carbonyl)amino]phenoxy}-2-pyridine carboxamide 1-oxide.
4-{4-[({[4-bromo-3-(trifluoromethyl)phenyl]amino}carbonyl)amino]phenoxy}-2-pyridine carboxamide 1-oxide.
4-{4-[({[4-chloro-3-(trifluoromethyl)phenyl]amino}carbonyl)amino]phenoxy}-N-hydroxymethyl-2-pyridine carboxamide 1-oxide.
4-{4-[({[4-bromo-3-(trifluoromethyl)phenyl]amino}carbonyl)amino]phenoxy}-N-hydroxymethyl-2-pyridine carboxamide 1-oxide, and salts, stereoisomers and prodrugs thereof.

A subgroup of the compounds of the invention which are of interest include compounds of formula (II), or a salt or stereoisomer thereof,

II wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$Z^1$ and $Z^2$ are each H or OH, wherein only one of $Z^1$ or $Z^2$ can be OH,
$X^4$ to $X^7$ are each, independently, H, OH or $O(CO)C_1$-$C_4$ alkyl, and
n is 0 or 1,
with the proviso that at least one of conditions a-c is met,
  a) $Z^1$ or $Z^2$ is OH,
  b) $R^2$ is OH,
  c) n is 1.

These include compounds of the invention wherein in formula (II) n is 1, compounds of the invention wherein in formula (II) n is 1 and $Z^1$ and $Z^2$ are each H, compounds of the invention wherein in formula (II) n is 1, $Z^1$ and $Z^2$ are H and at least one of $X^4$ to $X^7$ is OH, compounds of the invention wherein in formula (II) n is 1, $Z^1$ and $Z^2$ are H and Y is $NHR^2$ and $R^2$ is H or $CH_3$, compounds of the invention wherein in formula (II) n is 0, compounds of the invention wherein in formula (II) n is 0 and $Z^1$ is H and $Z^2$ is OH or $Z^1$ is OH and $Z^2$ is H, compounds of the invention wherein in formula (II) n is 0, $Z^1$ and $Z^2$ are each H, and at least one of $X^4$ to $X^7$ is OH, compounds of the invention wherein in formula (II) n is 0 and $Z^1$ is H and $Z^2$ is OH or $Z^1$ is OH and $Z^2$ is H and at least one of $X^4$ to $X^7$ is OH, compounds of the invention wherein in formula (II) n is 0 and $Z^1$ is H and $Z^2$ is OH or $Z^1$ is OH and $Z^2$ is H and Y is $NHR^2$ and $R^2$ is H or $CH_3$, compounds of the invention wherein in formula (II) n is 0 and $Z^1$ is H and $Z^2$ is OH or $Z^1$ is OH and $Z^2$ is H, Y is $NHR^2$ $R^2$ is OH, and compounds of the invention wherein in formula (II), Y is $NHR^2$, $R^2$ is OH, n is 0 and at least one of $X^4$ to $X^7$ is OH.

Another subgroup of the compounds of the invention which are of interest include compounds of formula (III), or a salt or isolated stereoisomer thereof,

III wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$Z^1$ and $Z^2$ are each H or OH, wherein only one of $Z^1$ or $Z^2$ can be OH, and
n is 0 or 1,
with the proviso that at least one of conditions a-c is met,
  a) $Z^1$ or $Z^2$ is OH,
  b) $R^2$ is OH,
  c) n is 1.

These include compounds of the invention wherein in formula (III) n is 1 and $Z^1$ and $Z^2$ are each H, compounds of the invention wherein in formula (III) n is 1, $Z^1$ and $Z^2$ are each H, Y is $NHR^2$ and $R^2$ is H or $CH_3$, compounds of the invention wherein in formula (III) n is 0 and $Z^1$ is H and $Z^2$ is OH or $Z^1$ is OH and $Z^2$ is H, compounds of the invention wherein in formula (III) n is 0, $Z^1$ is H and $Z^2$ is OH or $Z^1$ is OH and $Z^2$ is H, Y is $NHR^2$ and $R^2$ is H or $CH_3$, and compounds of the invention wherein in formula (III) Y is OH.

The invention further relates to processes and methods of preparing the novel compounds of the invention. Such processes and methods include, but are not limited to, the oxidation of the pyridyl ring of 4-{4-[({[4-chloro-3-(trifluoromethyl)phenyl]amino}carbonyl)amino]phenoxy}-N-methyl-2-pyridine carboxamide and 4-{4-[({[4-bromo-3-(trifluoromethyl)phenyl]amino}carbonyl)amino]phenoxy}-N-methyl-2-pyridine carboxamide into their corresponding pyridine-1-oxides, the formal oxidation of any of the urea nitrogens of compounds of the invention into an N-hydroxyurea, the oxidation of any of the positions represented by $X^1$ to $X^7$ of compounds of the invention whereby a hydrogen atom is replaced by a hydroxyl group, the hydroxylation of the N-methyl amides of 4-{4-[({[4-chloro-3-(trifluoromethyl)phenyl]amino}carbonyl)amino]phenoxy}-N-methyl-2-pyridine carboxamide and 4-{4-[({[4-bromo-3-(trifluoromethyl)phenyl]amino}carbonyl)amino]phenoxy}-N-methyl-2-pyridine carboxamide into the corresponding hydroxymethyl amides, the hydroxylation of said N-methyl amides into hydroxamic acids, the demethylation of said N-methyl amides into unsubstituted amides, the hydrolysis of said N-methyl amides into carboxylic acids and combinations thereof. Furthermore, the invention relates to the esterification of hydroxyl groups in the $X^1$ to $X^7$ positions to, for example, acetates.

Processes of interest include a process for preparing 4-{4-[({[4-chloro-3-(trifluoromethyl)phenyl]amino}carbonyl)amino]phenoxy}-N-methyl-2-pyridine carboxamide 1-oxide, or 4-{4-[({[4-bromo-3-(trifluoromethyl)phenyl]amino}carbonyl)amino]phenoxy}-N-methyl-2-pyridine carboxamide 1-oxide, or pharmaceutically acceptable salt, or an isolated stereoisomer thereof comprising oxidizing 4-{4-[({[4-chloro-3-(trifluoromethyl)phenyl]amino}carbonyl)amino]phenoxy}-N-methyl-2-pyridine carboxamide or 4-{4-[({[4-bromo-3-(trifluoromethyl)phenyl]amino}carbonyl)amino]phenoxy}-N-methyl-2-pyridine carboxamide into the corresponding pyridine-1-oxides and a process for preparing 4-{4-[({[4-chloro-3-(trifluoromethyl)phenyl]amino}carbonyl)amino]phenoxy}2-pyridine carboxamide 1-oxide, or 4-{4-[({[4-bromo-3-(trifluoromethyl)phenyl]amino}carbonyl)amino]phenoxy}2-pyridine carboxamide 1-oxide or pharmaceutically acceptable salt, or an isolated stereoisomer thereof comprising oxidizing 4-{4-[({[4-chloro-3-(trifluoromethyl)phenyl]amino}carbonyl)amino]phenoxy}-2-pyridine carboxamide or 4-{4-[({[4-bromo-3-(trifluoromethyl)phenyl]amino}carbonyl)amino]phenoxy}-2-pyridine carboxamide into the corresponding pyridine-1-oxides.

Compounds prepared by these methods are included in the invention. Also included are compounds obtained by transformation, including metabolic transformation, of 4-{4-[({[4-chloro-3-(trifluoromethyl)phenyl]amino}carbonyl)amino]phenoxy}-N-methyl-2-pyridine carboxamide or 4-{4-[({[4-bromo-3-(trifluoromethyl)phenyl]amino}carbonyl)amino]phenoxy}-N-methyl-2-pyridine carboxamide to either:

a) replace one or more of the phenyl hydrogens with a hydroxyl group,
b) hydroxyate the N-methyl amide into a hydroxymethyl amide or hydroxamic acid,
c) demethylate the N-methyl amide into an unsubstituted amide,
d) oxidize one or more of the urea nitrogens from =NH to =NOH,
e) hydrolyze the N-methyl amide into a carboxylic acid,
f) oxidize the pyridine nitrogen into a pyridine-1-oxide, or
g) a combination of a-f,
with the proviso that at least one of steps b), d), and f) is performed.

Of particular interest are compounds obtained by transformation, including metabolic transformation, of 4-{4-[({[4-chloro-3-(trifluoromethyl)phenyl]amino}carbonyl)amino]phenoxy}-N-methyl-2-pyridine carboxamide or 4-{4-[({[4-bromo-3-(trifluoromethyl)phenyl]amino}carbonyl)amino]phenoxy}-N-methyl-2-pyridine carboxamide to either:

a) hydroxyate the N-methyl amide into a hydroxymethyl amide or hydroxamic acid,
b) demethylate the N-methyl amide into an unsubstituted amide,
c) oxidize one or more of the urea nitrogens from =NH to =NOH,
d) hydrolyze the N-methyl amide into a carboxylic acid,
e) oxidize the pyridine nitrogen into a pyridine-1-oxide, or
f) a combination of a-e,
with the proviso that at least one of steps a), c), and e) is performed.

It is understood that the term "pyridine-1-oxide" used throughout the document includes 1-oxo-pyridine and 1-hydroxy-pyridine, and that for the purposes of this document, all 3 terms are considered interchangeable. For example, ChemInnovation Software, Inc. Nomenclator™ v. 3.01 identifies compounds of formula III where Y=NHCH$_3$, Hal=Cl, $Z^1$ and $Z^7$=H, and n=1, drawn in ChemDraw, as N-[4-chloro-3-(trifluoromethyl)phenyl]({4-[1-hydroxy-2-(N-methylcarbamoyl)(4-pyridyloxy)]phenyl}amino)carboxamide.

The invention further relates to a pharmaceutical composition comprising one or more compounds of the invention.

These include a pharmaceutical composition comprising an effective amount of at least one compound of the invention and a physiologically acceptable carrier. Preference is given to a pharmaceutical composition comprising an effective amount of 4-{4-[({[4-chloro-3-(trifluoromethyl)phenyl]amino}carbonyl)amino]phenoxy}-N-methyl-2-pyridine carboxamide 1-oxide, 4-{4-[({[4-bromo-3-(trifluoromethyl)phenyl]amino}carbonyl)amino]phenoxy}-N-methyl-2-pyridine carboxamide 1-oxide, 4-{4-[({[4-chloro-3-(trifluoromethyl)phenyl]amino}carbonyl)amino]phenoxy}2-pyridine carboxamide 1-oxide, or 4-{4-[({[4-bromo-3-(trifluoromethyl)phenyl]amino}carbonyl)amino]phenoxy}2-pyridine carboxamide 1-oxide or a pharmaceutically acceptable salt, an isolated stereoisomer or a mixture thereof and a physiologically acceptable carrier.

Pharmaceutically acceptable salts of these compounds are also within the scope of the invention.

Salts of this invention are especially the pharmaceutically acceptable salts of compounds of formula (I) such as, for example, organic or inorganic acid addition salts of compounds of formula (I). Suitable inorganic acids include but are not limited to halogen acids (such as hydrochloric acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, dodecanoic acid, glycolic acid, lactic acid, 2- or 3-hydroxybutyric acid, γ-aminobutyric acid (GABA), gluconic acid, glucosemonocarboxylic acid, fumaric acid, succinic acid, adipic acid, pimelic acid, suberic acid, azeiaic acid, malic acid, tartaric acid, citric acid, glucaric acid, galactaric acid, amino acids (such as glutamic acid, aspartic acid, N-methylglycine, acetytaminoacetic acid, N-acetylasparagine or N-acetylcysteine), pyruvic acid, acetoacetic acid, methanesulfonic acid, 4-toluene sulfonic acid, benzenesulfonic acid, phosphoserine, and 2- or 3-glycerophosphoric acid.

Formation of prodrugs is well known in the art in order to enhance the properties of the parent compound; such properties include solubility, absorption, biostability and release time (see *"Pharmaceutical Dosage Form and Drug Delivery Systems"* (Sixth Edition), edited by Ansel et al., published by Williams & Wilkins, pages 27-29, (1995) which is hereby incorporated by reference). Commonly used prodrugs of the disclosed oxazolyl-phenyl-2,4-diamino-pyrimidine compounds are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see *Goodman and Gilman's The Pharmacological Basis of Therapeutics* (Ninth Edition), editor Molinoff et al., publ. by McGraw-Hill, pages 11-13, (1996), which is hereby incorporated by reference).

The invention also relates to methods for treating and preventing diseases, for example, inflammatory and angiogenesis disorders and osteoporosis in mammals by administering a compound of the invention, or a pharmaceutical composition comprising a compound of the invention.

These include a method of treating or preventing osteoporosis, inflammation, and angiogenesis disorders (other than cancer) in a mammal by administering an effective amount of a compound of the invention to said mammal. Preference is given to a method of treating or preventing osteoporosis, inflammation, and angiogenesis disorders (other than cancer) in a mammal by administering an effective amount of 4-{4-[({[4-chloro-3-(trifluoromethyl)phenyl]amino}carbonyl)amino]phenoxy}-N-methyl-2-pyridine carboxamide 1-oxide, 4-{4-[({[4-bromo-3-(trifluoromethyl)phenyl]amino}carbonyl)amino]phenoxy}-N-methyl-2-pyridine carboxamide 1-oxide, 4-{4-[({[4-chloro-3-(trifluoromethyl)phenyl]amino}carbonyl)amino]phenoxy}2-pyridine carboxamide 1-oxide, or 4-{4-[({[4-bromo-3-(trifluoromethyl)phenyl]amino}carbonyl)amino]phenoxy}2-pyridine carboxamide 1-oxide or pharmaceutically acceptable salt, an isolated stereoisomer or a mixture thereof to said mammal.

The invention also relates to a method of treating or preventing cancer and other hyperproliferative disorders by administering a compound of the invention, or a pharmaceutical composition comprising one or more compounds of the invention, in combination with a cytotoxic agent.

These include a method of treating or preventing a hyper-proliferative disorder in a mammal by administering an effective amount of a compound of the invention to said mammal. Preference is given to a method of treating or preventing a hyper-proliferative disorder in a mammal by administering an effective amount of 4-{4-[({[4-chloro-3-(trifluoromethyl) phenyl]amino}carbonyl)amino]phenoxy}-N-methyl-2-pyridine carboxamide 1-oxide, 4-{4-[({[4-bromo-3-(trifluoromethyl)phenyl]amino}carbonyl)amino]phenoxy}-N-methyl-2-pyridine carboxamide 1-oxide, 4-{4-[({[4-chloro-3-(trifluoromethyl)phenyl]amino}carbonyl)amino]phenoxy}2-pyridine carboxamide 1-oxide, or 4-{4-[({[4-bromo-3-(trifluoromethyl)phenyl]amino}carbonyl)amino]phenoxy}2-pyridine carboxamide 1-oxide or a pharmaceutically acceptable salt, or an isolated stereoisomer or a mixture thereof to said mammal.

In the method of treating or preventing a hyper-proliferative disorder in a mammal by administering an effective amount of a compounds of the invention, one or more additional compounds or compositions may be administered to said mammal, such as for example, an anticancer compound or composition, which is not a compound or composition according to the invention, which is preferably a cytotoxic compound or composition. The method of treating or preventing a hyper-proliferative disorder in a mammal also includes administering an effective amount of 4-{4-[({[4-chloro-3-(trifluoromethyl)phenyl]amino}carbonyl)amino]phenoxy}-N-methyl-2-pyridine carboxamide 1-oxide, 4-{4-[({[4-bromo-3-(trifluoromethyl)phenyl]amino}carbonyl)amino]phenoxy}-N-methyl-2-pyridine carboxamide 1-oxide, 4-{4-[({[4-chloro-3-(trifluoromethyl)phenyl]amino}carbonyl)amino]phenoxy}2-pyridine carboxamide 1-oxide, or 4-{4-[({[4-bromo-3-(trifluoromethyl)phenyl]amino}carbonyl)amino]phenoxy}2-pyridine carboxamide 1-oxide or a pharmaceutically acceptable salt, or an isolated stereoisomer or a mixture thereof to said mammal together with a cytotoxic compound or composition.

Optional anti-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-proliferative agents suitable for use with the composition of the invention include but are not limited to other anti-cancer agents such as oxaliplatin, gemcitabone, gefinitib, taxotere, BCNU, CCNU, DTIC, ara A, ara C, herceptin, actinomycin D, epothilone, irinotecan, raloxifen and topotecan.

Description of Treatment of Hyperproliferative Disorders

Cancer and hyperproliferative disorders are defined as follows. These disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in man, but also exist with a similar etiology in other mammals, and can be treated by pharmaceutical compositions of the present invention.

Generally, the use of cytotoxic and/or cytostatic agents in combination with aryl urea compound raf kinase inhibitors will serve to (1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

The present invention relates to a combination comprising (a) a compound according to the invention (b) at least one other chemotherapeutic cytotoxic or cytostatic agent; or pharmaceutically acceptable salts of any component (a) or (b).

The invention also relates to a pharmaceutical preparation which comprises (1) quantities of (a) a compound according to the invention (b) at least one other cytotoxic or cytostatic agent in amounts which are jointly effective for treating a cancer, where any component (a) or (b) can also be present in the form of a pharmaceutically acceptable salt if at least one salt-forming group is present, with (2) one or more pharmaceutically acceptable carrier molecules.

The invention also relates to a method for treating a cancer that can be treated by administration of a compound according to the invention and at least one other chemotherapeutic agent which is a cytotoxic or cytostatic agent. The compound according to the invention and the cytotoxic or cytostatic agent are administered to a mammal in quantities which together are therapeutically effective against hyper proliferative diseases as defined above. Thus, the compound according to the invention is effective for raf kinase-mediated cancers. However, these compounds are also effective for cancers not mediated by raf kinase.

In a preferred embodiment, the present invention provides methods for treating a cancer in a mammal, especially a human patient, comprising administering an a compound according to the invention optionally in combination with a cytotoxic or cytostatic chemotherapeutic agent including but not limited to DNA topoisomerase I and II inhibitors, DNA intercalators, alkylating agents, microtubule disruptors, hormone and growth factor receptor agonists or antagonists, other kinase inhibitors and antimetabolites.

In another embodiment, a method is disclosed for administering the chemotherapeutic agents, including a compound according to the invention and the cytotoxic and cytostatic agents, to the patient by oral delivery or by intravenous injection or infusion.

In another embodiment, the composition comprising a compound according to the invention or the cytotoxic or cytostatic agent can be administered to a patient in the form of a tablet, a liquid, a topical gel, an inhaler or in the form of a sustained release composition.

In one embodiment of the invention, a compound according to the invention can be administered simultaneously with a cytotoxic or cytostatic agent to a patient with a cancer, in the same formulation or, more typically in separate formulations and, often, using different administration routes. Administration can also be sequentially, in any order.

In another embodiment, a compound according to the invention can be administered in tandem with the cytotoxic or cytostatic agent, wherein a compound according to the invention can be administered to a patient once or more per day for up to 28 consecutive days with the concurrent or intermittent administration of a cytotoxic or cytostatic agent over the same total time period.

In another embodiment of the invention, a compound according to the invention can be administered to a patient at an oral, intravenous, intramuscular, subcutaneous, or parenteral dosage which can range from about 0.1 to about 200 mg/kg of total body weight.

In another embodiment, the cytotoxic or cytostatic agent can be administered to a patient at an intravenous, intramuscular, subcutaneous, or parenteral dosage which can range from about 0.1 mg to 200 mg/kg of patient body weight.

Further, the invention relates to a method of inhibiting proliferation of cancer cells comprising contacting cancer cells with a pharmaceutical preparation or product of the invention, especially a method of treating a proliferative disease comprising contacting a subject, cells, tissues or a body fluid of said subject, suspected of having a cancer with a pharmaceutical composition or product of this invention.

This invention also relates to compositions containing both a compound according to the invention and the other cytotoxic or cytostatic agents, in the amounts of this invention.

This invention further relates to kits comprising separate doses of the two mentioned chemotherapeutic agents in separate containers. The combinations of the invention can also be formed in vivo, e.g., in a patient's body.

The term "cytotoxic" refers to an agent which can be administered to kill or eliminate a cancer cell. The term "cytostatic" refers to an agent which can be administered to restrain tumor proliferation rather than induce cytotoxic cytoreduction yielding an elimination of the cancer cell from the total viable cell population of the patient. The chemotherapeutic agents described herein, e.g., irinotecan, vinorelbine, gemcitabine, and paclitaxel are considered cytotoxic agents. These cytotoxic and cytostatic agents have gained wide spread use as chemotherapeutics in the treatment of various cancer types and are well known.

These and other cytotoxic/cytostatic agents can be administered in the conventional formulations and regimens in which they are known for use alone.

GENERAL PREPARATIVE METHODS

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in Examples 1 and 2.

Ureas and hydroxyureas of formula (I) can be prepared by a variety of simple methods known in the art. General approaches for the formation of those compounds can be found in "*Advanced Organic Chemistry*", by J. March, John Wiley and Sons, 1985 and in "*Comprehensive Organic Transformations*", by R. C. Larock, *VCH Publishers*, 1989), which are hereby incorporated by reference.

More specifically, the pyridine-1-oxides (n=1 in Formula (I)) of the present invention can be prepared from the corresponding pyridines using oxidation conditions known in the art. Some examples are as follows:

peracids such as meta chloroperbenzoic acids in chlorinated solvents such as dichloromethane, dichloroethane, or chloroform (Markgraf et al., *Tetrahedron* 1991, 47, 183).

$(Me_3SiO)_2$ in the presence of a catalytic amount of perrhenic acid in chlorinated solvents such as dichloromethane (Coperet et al., *Tetrahedron Lett.* 1998, 39, 761)

Perfluoro-cis-2-butyl-3-propyloxaziridine in several combinations of halogenated solvents (Amone et al., *Tetrahedron* 1998, 54, 7831).

Hypofluoric acid—acetonitrile complex in chloroform (Dayan et al., *Synthesis* 1999, 1427).

Oxone, in the presence of a base such as KOH, in water (Robker et al., *J. Chem. Res., Synop.* 1993, 10, 412).

Magnesium monoperoxyphthalate, in the presence of glacial acetic acid (Klemm et al., *J. Heterocyclic Chem.* 1990, 6, 1537).

Hydrogen peroxide, in the presence of water and acetic acid (Lin A. J., *Org. Prep. Proced. Int.* 1991, 23(1), 114).

Dimethyldioxirane in acetone (Boyd et al., *J. Chem. Soc., Perkin Trans.* 1991, 9, 2189).

The starting materials for the above-mentioned oxidations are bis aryl ureas, which contain a 2-acyl-pyridine in their side chains. Specific preparations of these ureas are already described in the patent literature, and can be adapted to the compounds of the present invention. For example, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698.

Hydroxyureas of formula (I), where $Z^1$ is OH and $Z^2$ is H can be prepared as follows:

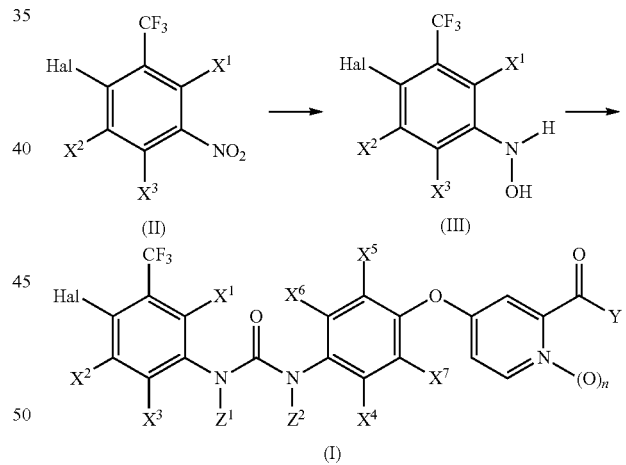

Substituted nitrobenzenes of Formula (II), which are known in the art, are converted to hydroxyanilines of Formula (III), using a variety of conditions known in the art, for example sodium borohydride in the presence of transition metal catalysts (Yanada et al., *Chem. Lett.* 1989, 951 and references cited therein), or N-methyldihydroacridine in the presence of perchloric acid (Fukuzumi et al., *J. Chem. Soc., Perkin Trans. II* 1991, 9, 1393, and references cited therein).

In the second step, hydroxyanilines of Formula (III) can be converted to the corresponding hydroxyureas by reaction with an isocyanate, or equivalent, in the same way ureas are being prepared. Examples of such reactions can be found in the art (Hoffman et al., *J. Med. Chem.* 1964, 7, 665, and Stoffel et al., *Ber. Dtsch. Chem. Ges.* 1972, 105, 3115).

Similarly, hydroxyureas of formula (I), where $Z^1$ is H and $Z^2$ is OH can be prepared according to the same methods, by substituting the reagents in the appropriate way.

In both cases, the preparation of the arylamine fragment is illustrated in detail in the patent literature. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using. Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698.

Hydroxymethyl amides of Formula (I) where Y is $NHCH_2OH$ can be prepared by hydroxylation of the corresponding unsubstituted amides ($Y=NH_2$) by a variety of methods known in the art, for example aqueous formaldehyde in the presence of ethanol and sodium hydroxide (Weaver et al., *J. Org. Chem.* 1951, 16, 1111), or in the presence of potassium carbonate (Haworth et al., *J. Chem. Soc.* 1946, 1003).

Hydroxamic acids of Formula (I) where Y is NHOH can be prepared by amidation of the corresponding esters (Y=O alkyl) by a variety of methods known in the art, for example hydroxylamine in the presence of acetic acid and water (Boshagen, H., *Ber. Dtsch. Chem. Ges.* 1967, 100, 954). The same compounds can be obtained from the corresponding acids (Y=OH) by one pot activation of the acid with ethyl chloroformate, followed by reaction with hydroxylamine in methanol (Reddy et al., *Tetrahedron Lett.* 2000, 41(33), 6285), or by activation of the acid into an 1-acylimidazole, followed by reaction with hydroxylamine hydrochloride (Staab et al., *Angewandte Chem.*, 1962, 74, 407).

Finally, ureas may be further manipulated using methods familiar to those skilled in the art.

The invention also includes pharmaceutical compositions including a compound of the invention, and a physiologically acceptable carrier.

The compounds may be administered orally, topically, parenterally, by injection, by inhalation or spray or rectally in dosage unit formulations. Administration by injection includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For all regimens of use disclosed herein for compounds of the invention, the daily oral dosage regimen will preferably be from 0.01 to 200 mg/kg of total body weight. The daily dosage for administration by injection, including intravenous, intramuscular, subcutaneous and parenteral injections, and use of infusion techniques will preferably be from 0.01 to 200 mg/kg of total body weight. The daily rectal dosage regime will preferably be from 0.01 to 200 mg/kg of total body weight. The daily topical dosage regime will preferably be from 0.1 to 200 mg administered between one to four times daily. The daily inhalation dosage regime will preferably be from 0.01 to 10 mg/kg of total body weight. The dosage units employed to provide these dosage regimes can be administered on a daily basis, one or more times, or for extended periods, such as on a weekly or monthly basis.

It will be appreciated by those skilled in the art that the particular method of administration will depend on a variety of factors, all of which are considered routinely when administering therapeutics. It will also be appreciated by one skilled in the art that the specific dose level for a given patient depends on a variety of factors, including specific activity of the compound administered, age, body weight, health, sex, diet, time and route of administration, rate of excretion, etc. It will be further appreciated by one skilled in the art that the optimal course of treatment, i.e., the mode of treatment and the daily number of doses of a compound of the invention for a defined number of days, can be ascertained by those skilled in the art using conventional treatment tests.

The compounds can be produced from known compounds (or from starting materials which, in turn, can be produced from known compounds), e.g., through the general preparative methods disclosed herein. The activity of a given compound to inhibit raf, p38, or KDR (VEGFR2) kinases can be routinely assayed, e.g., according to procedures disclosed herein.

The entire enclosure of all applications, patents and publications cited above and below are hereby incorporated by reference, including non-provisional application Ser. No. 09/425,228 filed Oct. 22, 1999, and non-provisional application Ser. No. 09/458,548 filed Jan. 12, 2001.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg. Unless otherwise stated, the term 'under high vacuum' refers to a vacuum of 0.4-1.0 mmHg.

All temperatures are reported uncorrected in degrees Celsius (° C.). Unless otherwise indicated, all parts and percentages are by weight. Commercial grade reagents and solvents were used without further purification.

Thin-layer chromatography (TLC) is performed using Whatman® pre-coated glass-backed silica gel 60A F-254 250 µm plates. Visualization of plates is effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) is performed using 230-400 mesh EM Science® silica gel.

Melting points (mp) are determined using a Thomas-Hoover melting point apparatus or a Mettler FP66 automated melting point apparatus and are uncorrected. Fourier transform infrared spectra are obtained using a Mattson 4020 Galaxy Series spectrophotometer. Proton ($^1$H) nuclear magnetic resonance (NMR) spectra are measured with a General Electric GN-Omega 300 (300 MHz) spectrometer with either Me$_4$Si ($\delta$ 0.00) or residual protonated solvent (CHCl$_3$ $\delta$ 7.26; MeOH $\delta$ 3.30; DMSO $\delta$ 2.49) as standard. Carbon ($^{13}$C) NMR spectra are measured with a General Electric GN-Omega 300 (75 MHz) spectrometer with solvent (CDCl$_3$ $\delta$ 77.0; MeOD-d$_3$; $\delta$ 49.0; DMSO-d$_6$ $\delta$ 39.5) as standard. Low resolution mass spectra (MS) and high resolution mass spectra (HRMS) are either obtained as electron impact (EI) mass spectra or as fast atom bombardment (FAB) mass spectra. Electron impact mass spectra (EI-MS) are obtained with a Hewlett Packard 5989A mass spectrometer equipped with a Vacumetrics Desorption Chemical Ionization Probe for sample introduction. The ion source is maintained at 250° C. Electron impact ionization is performed with electron energy of 70 eV and a trap current of 300 µA. Liquid-cesium secondary ion mass spectra (FAB-MS), an updated version of fast atom bombardment are obtained using a Kratos Concept 1-H spectrometer. Chemical ionization mass spectra (CI-MS) are obtained using a Hewlett Packard MS-Engine (5989A) with methane or ammonia as the reagent gas ($1 \times 10^{-4}$ torr to $2.5 \times 10^{-4}$ torr). The direct insertion desorption chemical ionization (DCI) probe (Vaccumetrics, Inc.) is ramped from 0-1.5 amps in 10 sec and held at 10 amps until all traces of the sample disappeared (~1-2 min). Spectra are scanned from 50-800 amu at 2 sec per scan. HPLC—electrospray mass spectra (HPLC ES-MS) are obtained using a Hewlett-Packard 1100 HPLC equipped with a quaternary pump, a variable wavelength detector, a C-18 column, and a Finnigan LCQ ion trap mass spectrometer with electrospray ionization. Spectra are scanned from 120-800 amu using a variable ion time according to the number of ions in the source. Gas chromatography—ion selective mass spectra (GC-MS) are obtained with a Hewlett Packard 5890 gas chromatograph equipped with an HP-1 methyl silicone column (0.33 mM coating; 25 m—0.2 mm) and a Hewlett Packard 5971 Mass Selective Detector (ionization energy 70 eV). Elemental analyses are conducted by Robertson Microlit Labs, Madison N.J.

All compounds displayed NMR spectra, LRMS and either elemental analysis or HRMS consistent with assigned structures.

Example 1

Preparation of N-[4-chloro-3-(trifluoromethyl)phenyl]-N'-{4-[2-(N-methylcarbamoyl)-1-oxo-(4-pyridyloxy)]phenyl}urea

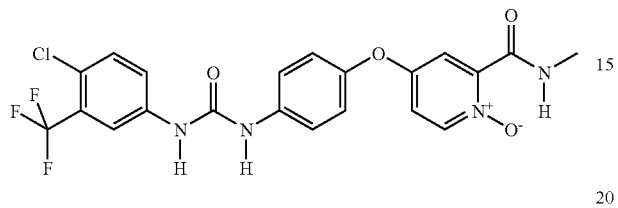

To a stirred mixture of N-[4-chloro-3-(trifluoromethyl)phenyl]-N'-{4-[2-(N-methylcarbamoyl)(4-pyridyloxy)]phenyl}urea (500 mg, 1.08 mmol), in a mixture of anh $CH_2Cl_2$ (2.2 mL) and anh THF (2.2 mL) was added 3-chloroperbenzoic acid (77% pure, 1.09 g, 4.86 mmol, 4.5 equiv.), and the resulting mixture was heated at 40° C. for 33 h. The resulting mixture was concentrated under reduced pressure, and the crude product was purified by MPLC (Biotage®; gradient from 20% acetone/hexane to 50% acetone/hexane). Recrystallization from EtOAc afforded N-[4-chloro-3-(trifluoromethyl)phenyl]-N'-{4-[2-(N-methylcarbamoyl)-1-oxo-(4-pyridyloxy)]phenyl}urea as a white solid (293 mg, 57%): mp (uncorrected) 232-234° C.; TLC (50% acetone/hexane) $R_f$ 0.13; $^1$H-NMR (DMSO-$d_6$) δ 11.48 (broad s, 1H), 9.19 (s, 1H), 8.98 (s, 1H), 8.38 (d, J=5.8 Hz, 1H), 8.10 (d, J=2.5 Hz, 1H), 7.64 (dd, J=8.2 Hz, 2.6 Hz, 1H), 7.61 (d, J=8.4 Hz, 1H), 7.57 (d, J=8.7 Hz, 2H), 7.54 (d, J=2.6 Hz, 1H), 7.28 (dd, J=5.7 Hz, 2.5 Hz, 1H), 7.18 (d, J=8.8 Hz, 2H), 2.86 (d, J=5.0 Hz, 3H); HPLC EI-MS m/z 481 ((M+H)$^+$). Anal. calcd for $C_{21}H_{16}ClFN_4O_4$: C, 52.46%; H, 3.33%; N, 11.65%. Found: C, 52.22%; H, 3.39%; N, 11.49%.

Example 2

Preparation of N-[4-chloro-3-(trifluoromethyl)phenyl]-N'-{4-[2-carbamoyl-1-oxo-(4-pyridyloxy)]phenyl}urea

Step 1: Preparation of 4-chloro-2-pyridinecarboxamide

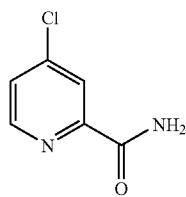

To a stirred mixture of methyl 4-chloro-2-pyridinecarboxylate hydrochloride (1.0 g, 4.81 mmol) dissolved in conc. aqueous ammonia (32 mL) was added ammonium chloride (96.2 mg, 1.8 mmol, 0.37 equiv.), and the heterogeneous reaction mixture was stirred at ambient temperature for 16 h. The reaction mixture was poured into EtOAc (500 mL) and water (300 mL). The organic layer was washed with water (2×300 mL) and a saturated NaCl solution (1×300 mL), dried (MgSO$_4$), concentrated in vacuo to give 4-chloro-2-pyridinecarboxamide as a beige solid (604.3 mg, 80.3%): TLC (50% EtOAc/hexane) $R_f$ 0.20; $^1$H-NMR (DMSO-$d_6$) δ 8.61 (d, J=5.4 Hz, 1H), 8.20 (broad s, 1H), 8.02 (d, J=1.8 Hz, 1H), 7.81 (broad s, 1H), 7.76 to 7.73 (m, 1H).

Step 2: Preparation of 4-(4-aminophenoxy)-2-pyridinecarboxamide

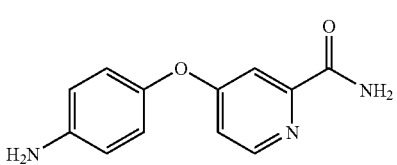

To 4-aminophenol (418 mg, 3.83 mmol) in anh DMF (7.7 mL) was added potassium tert-butoxide (447 mg, 3.98 mmol, 1.04 equiv.) in one portion. The reaction mixture was stirred at room temperature for 2 h, and a solution of 4-chloro-2-pyridinecarboxamide (600 mg, 3.83 mmol, 1.0 equiv.) in anh DMF (4 mL) was then added. The reaction mixture was stirred at 80° C. for 3 days and poured into a mixture of EtOAc and a saturated NaCl solution. The organic layer was sequentially washed with a saturated NH$_4$Cl solution then a saturated NaCl solution, dried (MgSO$_4$), and concentrated under reduced pressure. The crude product was purified using MPLC chromatography (Biotage®; gradient from 100% EtOAc to followed by 10% MeOH/50% EtOAc/40% hexane) to give the 4-chloro-5-trifluoromethylaniline as a brown solid (510 mg, 58%). $^1$H-NMR (DMSO-$d_6$) δ 8.43 (d, J=5.7 Hz, 1H), 8.07 (br s, 1H), 7.66 (br s, 1H), 7.31 (d, J=2.7 Hz, 1H), 7.07 (dd, J=5.7 Hz, 2.7 Hz, 1H), 6.85 (d, J=9.0 Hz, 2H), 6.62 (d, J=8.7 Hz, 2H), 5.17 (broad s, 2H); HPLC EI-MS m/z 230 ((M+H)$^+$).

Step 3: Preparation of N-[4-chloro-3-(trifluoromethyl)phenyl]-N'-{4-[2-carbamoyl-(4-pyridyloxy)]phenyl}urea

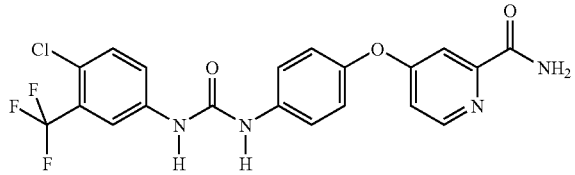

A mixture of 4-chloro-5-trifluoromethylaniline (451 mg, 2.31 mmol, 1.1 equiv.) and 1,1'-carbonyl diimidazole (419 mg, 2.54 mmol, 1.2 equiv.) in anh dichloroethane (5.5 mL) was stirred under argon at 65° C. for 16 h. Once cooled to room temperature, a solution of 4-(4-aminophenoxy)-2-pyridinecarboxamide (480 mg, 2.09 mmol) in anh THF (4.0 mL) was added, and the reaction mixture was stirred at 60° C. for 4 h. The reaction mixture was poured into EtOAc, and the organic layer was washed with water (2×) and a saturated NaCl solution (1×), dried (MgSO$_4$), filtered, and evaporated in vacuo. Purification using MPLC chromatography (Biotage®; gradient from 100% EtOAc to 2% MeOH/

EtOAc) gave N-[4-chloro-3-(trifluoromethyl)phenyl]-N'-{4-[2-carbamoyl-(4-pyridyloxy)]phenyl}urea as a white solid (770 mg, 82%): TLC (EtOAc) $R_f$ 0.11, 100% ethyl acetate $^1$H-NMR (DMSO-$d_6$) δ 9.21 (s, 1H), 8.99 (s, 1H), 8.50 (d, J=5.6 Hz, 1H), 8.11 (s, 1H), 8.10 (s, 1H), 7.69 (broad s, 1H), 7.64 (dd, J=8.2 Hz, 2.1 Hz, 1H), 7.61 (s, 1H), 7.59 (d, J=8.8 Hz, 2H), 7.39 (d, J=2.5 Hz, 1H), 7.15 (d, J=8.9 Hz, 2H), 7.14 (m, 1H); MS LC-MS (MH$^+$=451). Anal. calcd for $C_{20}H_{14}ClF_3N_4O_3$: C, 53.29%; H, 3.13%; N, 12.43%. Found: C, 53.33%; H, 3.21%; N, 12.60%.

Step 4: Preparation of N-[4-chloro-3-(trifluoromethyl)phenyl]-N'-{4-[2-carbamoyl-1-oxo-(4-pyridyloxy)]phenyl}urea

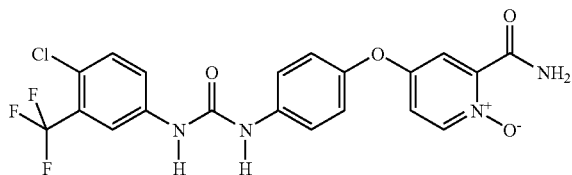

N-[4-chloro-3-(trifluoromethyl)phenyl]-N'-{4-[2-carbamoyl-1-oxo-(4-pyridyloxy)]phenyl}urea (125.6 mg, 51%) was prepared as a white solid from N-[4-chloro-3-(trifluoromethyl)phenyl]-N'-{4-[2-carbamoyl-(4-pyridyloxy)]phenyl}urea (240.0 mg, 0.53 mmol), in the manner described for N-[4-chloro-3-(trifluoromethyl)phenyl]-N'-{4-[2-(N-methylcarbamoyl)-1-oxo-(4-pyridyloxy)]phenyl}urea: TLC (5% MeOH/$CH_2Cl_2$) $R_f$ 0.17; $^1$H-NMR (DMSO-$d_6$) δ 10.72 (d, J=4.3 Hz, 1H), 9.21 (s, 1H), 8.99 (s, 1H), 8.36 (d, J=7.2 Hz, 1H), 8.31 (d, J=4.1 Hz, 1H), 8.10 (d, J=2.3 Hz, 1H), 7.65 (dd, J=8.7 Hz, 2.3 Hz, 1H), 7.60 (d, J=8.9 Hz, 1H), 7.57 (d, J=9.0 Hz, 2H), 7.54 (d, J=3.8 Hz, 1H), 7.28 (dd, J=7.2 Hz, 3.8 Hz, 1H), 7.18 (d, J=9.0 Hz, 2H); HPLC EI-MS m/z 467 ((M+H)$^+$; Anal. calcd for $C_{20}H_{14}ClF_3N_4O_4$ 0.5$H_2O$: C, 50.49%; H, 3.18%; N, 11.78%. Found. C, 50.69%; H, 2.86%; N, 11.47%.

BIOLOGICAL EXAMPLES

P38 Kinase In Vitro Assay:

The in vitro inhibitory properties of compounds were determined using a p38 kinase inhibition assay. P38 activity was detected using an in vitro kinase assay run in 96-well microtiter plates. Recombinant human p38 (0.5 μg/mL) was mixed with substrate (myelin basic protein, 5 μg/mL) in kinase buffer (25 mM Hepes, 20 mM $MgCl_2$ and 150 mM NaCl) and compound. One μCi/well of $^{33}$P-labeled ATP (10 μM) was added to a final volume of 100 μL. The reaction was run at 32° C. for 30 min. and stopped with a 1M HCl solution. The amount of radioactivity incorporated into the substrate was determined by trapping the labeled substrate onto negatively charged glass fiber filter paper using a 1% phosphoric acid solution and read with a scintillation counter. Negative controls include substrate plus ATP alone.

LPS Induced TNFα Production in Mice:

The in vivo inhibitory properties of selected compounds can be determined using a murine LPS induced TNFα production in vivo model. BALB/c mice (Charles River Breeding Laboratories; Kingston, N.Y.) in groups of ten were treated with either vehicle or compound by the route noted. After one hour, endotoxin (*E. coli* lipopolysaccharide (LPS) 100 μg) was administered intraperitoneally (i.p.). After 90 min, animals were euthanized by carbon dioxide asphyxiation and plasma was obtained from individual animals by cardiac puncture into heparinized tubes. The samples were clarified by centrifugation at 12,500×g for 5 min at 4° C. The supernatants were decanted to new tubes, which were stored as needed at −20° C. TNFα levels in sera were measured using a commercial murine TNF ELISA kit (Genzyme).

The two preceding biological examples can be used to demonstrate that the compounds are inhibiting p38 kinase in vitro and in vivo, and therefore establishes their utility in the treatment of p38 mediated diseases, such as inflammation and osteoporosis.

In Vitro raf Kinase Assay:

In an in vitro kinase assay, raf was incubated with MEK in 20 mM Tris-HCl, pH 8.2 containing 2 mM 2-mercaptoethanol and 100 mM NaCl. This protein solution (20 μL) was mixed with water (5 μL) or with compounds diluted with distilled water from 10 mM stock solutions of compounds dissolved in DMSO. The kinase reaction was initiated by adding 25 μL [γ-$^{33}$P]ATP (1000-3000 dpm/pmol) in 80 mM Tris-HCl, pH 7.5, 120 mM NaCl, 1.6 mM DTT, 16 mM $MgCl_2$. The reaction mixtures were incubated at 32° C., usually for 22 min. Incorporation of $^{33}$P into protein was assayed by harvesting the reaction onto phosphocellulose mats, washing away free counts with a 1% phosphoric acid solution and quantitating phosphorylation by liquid scintillation counting. For high throughput screening, 10 μM ATP and 0.4 μM MEK are used. In some experiments, the kinase reaction is stopped by adding an equal amount of Laemmli sample buffer. Samples are boiled 3 min and the proteins resolved by electrophoresis on 7.5% Laemmli gels. Gels were fixed, dried and exposed to an imaging plate (Fuji). Phosphorylation was analyzed using a Fujix Bio-Imaging Analyzer System. Compounds of Examples 1 and 2 show >50% inhibition at 10 micromolars in this assay, which is a marked inhibition of raf kinase in vitro.

Tumor Cell Proliferation Assay:

For in vitro growth assay, human tumor cell lines, including but not limited to HCT 116 and DLD-1, containing mutated K-ras genes were used in standard proliferation assays for anchorage dependent growth on plastic or anchorage independent growth in soft agar. Human tumor cell lines were obtained from ATCC (Rockville Md.) and maintained in RPMI with 10% heat inactivated fetal bovine serum and 200 mM glutamine. Cell culture media and additives were obtained from Gibco/BRL (Gaithersburg, Md.) except for fetal bovine serum (JRH Biosciences, Lenexa, Kans.). In a standard proliferation assay for anchorage dependent growth, 3×10$^3$ cells were seeded into 96-well tissue culture plates and allowed to attach overnight at 37° C. in a 5% $CO_2$ incubator. Compounds were titrated in media in dilution series and added to 96 well cell cultures. Cells were allowed to grow 5 days typically with a feeding of fresh compound containing media on day three. Proliferation was monitored by measuring metabolic activity with standard XTT colorimetric assay (Boehringer Mannheim) measured by standard ELISA plate reader at OD 490/560, harvesting the cells onto glass fiber mats using a cell harvester and measuring $^3$H-thymidine incorporation by liquid scintillant counting.

For anchorage independent cell growth, cells were plated at 1×10$^3$ to 3×10$^3$ in 0.4% Seaplaque agarose in RPMI complete media, overlaying a bottom layer containing only 0.64% agar in RPMI complete media in 24-well tissue culture plates. Complete media plus dilution series of compounds were added to wells and incubated at 37° C. in a 5% $CO_2$ incubator for 10-14 days with repeated feedings of fresh media containing compound at 3-4 day intervals. Colony formation was monitored and total cell mass, average colony size and number of colonies were quantitated using image capture technology and image analysis software (Image Pro Plus, media Cybernetics).

The two preceding assays establish that the compounds of Formula I are active to inhibit raf kinase activity and to inhibit oncogenic cell growth.

KDR (VEGFR2) Assay:

The cytosolic kinase domain of KDR kinase is expressed as a 6His fusion protein in Sf9 insect cells. The KDR kinase domain fusion protein is purified over a Ni++ chelating column. Ninety-six well ELISA plates are coated with 5 µg poly(Glu4; Tyr1) (Sigma Chemical Co., St Louis, Mo.) in 100 µl HEPES buffer (20 mM HEPES, pH 7.5, 150 mM NaCl, 0.02% Thimerosal) at 4° overnight. Before use, the plate is washed with HEPES, NaCl buffer and the plates are blocked with 1% BSA, 0.1% Tween 20 in HEPES, NaCl buffer.

Test compounds are serially diluted in 100% DMSO from 4 mM to 0.12 µM in half-log dilutions. These dilutions are further diluted twenty fold in H2O to obtain compound solutions in 5% DMSO. Following loading of the assay plate with 85 µl of assay buffer (20 mM HEPES, pH 7.5, 100 mM KCl, 10 mM $MgCl_2$, 3 mM $MnCl_2$, 0.05% glycerol, 0.005% Triton X-100, 1 mM -mercaptoethanol, with or without 3.3 µM ATP), 5 µl of the diluted compounds are added to a final assay volume of 100 µl. Final concentrations are between 10 µM, and 0.3 nM in 0.25% DMSO. The assay is initiated by the addition of 10 µl (30 ng) of KDR kinase domain.

The assay is incubated with test compound or vehicle alone with gentle agitation at room temperature for 60 minutes. The wells are washed and phosphotyrosines (PY) are probed with an anti-phosphotyrosine (PY), mAb clone 4G10 (Upstate Biotechnology, Lake Placid, N.Y.). PY/anti-PY complexes are detected with an anti-mouse IgG/HRP conjugate (Amersham International plc, Buckinghamshire, England). Phosphotyrosine is quantitated by incubating with 100 µl 3, 3', 5, 5' tetramethylbenzidine solution (Kirkegaard and Perry, TMB Microwell 1 Component peroxidase substrate). Color development is arrested by the addition of 100 µl 1% HCl-based stop solution (Kirkegaard and Perry, TMB 1 Component Stop Solution).

Optical densities are determined spectrophotometrically at 450 nm in a 96-well plate reader, SpectraMax 250 (Molecular Devices). Background (no ATP in assay) OD values are subtracted from all ODs and the percent inhibition is calculated according to the equation:

$$\% \text{ Inhibition} = \frac{(OD(\text{vehicle control}) - OD(\text{with compound})) \times 100}{OD(\text{vehicle control}) - OD(\text{no } ATP \text{ added})}$$

The $IC_{50}$ values are determined with a least squares analysis program using compound concentration versus percent inhibition.

Cell Mechanistic Assay-Inhibition of 3T3 KDR Phosphorylation:

NIH3T3 cells expressing the full length KDR receptor are grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ml of G418 (Life Technologies Inc., Grand Island, N.Y.). The cells are maintained in collagen I-coated T75 flasks (Becton Dickinson Labware, Bedford, Mass.) in a humidified 5% CO2 atmosphere at 37° C.

Fifteen thousand cells are plated into each well of a collagen I-coated 96-well plate in the DMEM growth medium. Six hours later, the cells are washed and the medium is replaced with DMEM without serum. After overnight culture to quiesce the cells, the medium is replaced by Dulbecco's phosphate-buffered saline (Life Technologies Inc., Grand Island, N.Y.) with 0.1% bovine albumin (Sigma Chemical Co., St Louis, Mo.). After adding various concentrations (0-300 nM) of test compounds to the cells in 1% final concentration of DMSO, the cells are incubated at room temperature for 30 minutes. The cells are then treated with VEGF (30 ng/ml) for 10 minutes at room temperature. Following VEGF stimulation, the buffer is removed and the cells are lysed by addition of 150 µl of extraction buffer (50 mM Tris, pH 7.8, supplemented with 10% glycerol, 50 mM BGP, 2 mM EDTA, 10 mM NaF, 0.5 mM NaVO4, and 0.3% TX-100) at 4° C. for 30 minutes.

To assess receptor phosphorylation, 100 microliters of each cell lysate is added to the wells of an ELISA plate precoated with 300 ng of antibody C20 (Santa Cruz Biotechnology, Inc., Santa Cruz, Calif.). Following a 60-minute incubation, the plate is washed and bound KDR is probed for phosphotyrosine using an anti-phosphotyrosine mAb clone 4G10 (Upstate Biotechnology, Lake Placid, N.Y.). The plate is washed and wells are incubated with anti-mouse IgG/HRP conjugate (Amersham International plc, Buckinghamshire, England) for 60 minutes. Wells are washed and phosphotyrosine is quantitated by addition of 100 µl per well of 3,3',5,5' tetramethylbenzidine (Kirkegaard and Perry, TMB Microwell 1 Component peroxidase substrate) solution. Color development is arrested by the addition of 100 µl 1% HCl based stop solution (Kirkegaard and Perry, TMB 1 Component Stop Solution).

Optical densities (OD) are determined spectrophotometrically at 450 nm in a 96-well plate reader (SpectraMax 250, Molecular Devices). Background (no VEGF added) OD values are subtracted from all ODs and percent inhibition is calculated according to the equation:

$$\% \text{ Inhibition} = \frac{(OD(VEGF \text{ control}) - OD(\text{with test compound})) \times 100}{OD(VEGF \text{ control}) - OD(\text{no } VEGF \text{ added})}$$

$IC_{50}$s are determined on some of the exemplary materials with a least squares analysis program using compound concentration versus percent inhibition.

In Vivo Assay of VEGFR Inhibition: Matrigel® Angiogenesis Model:

Preparation of Matrigel Plugs and in vivo Phase: Matrigel® (Collaborative Biomedical Products, Bedford, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. is mixed with SK-MEL2 human tumor cells that are transfected with a plasmid containing the murine VEGF gene with a selectable marker. Tumor cells are grown in vitro under selection and cells are mixed with cold liquid Matrigel at a ratio of $2 \times 10^6$ per 0.5 ml. One half milliliter is implanted subcutaneously near the abdominal midline using a 25 gauge needle. Test compounds are dosed as solutions in Ethanol/Cremaphor EL/saline (12.5%:12.5%:75%) at 30, 100, and 300 mg/kg po once daily starting on the day of implantation. Mice are euthanized 12 days post-implantation and the Matrigel pellets are harvested for analysis of hemoglobin content.

Hemoglobin Assay: the Matrigel pellets are placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete, EDTA-free protease inhibitor cocktail [Mannheim, Germany]), and homogenized at 4° C. Homogenates are incubated on ice for 30 minutes with shaking and centrifuged at 14K×g for 30 minutes at 4° C. Supernatants are transferred to chilled microfuge tubes and stored at 4° C. for hemoglobin assay.

Mouse hemoglobin (Sigma Chemical Co., St. Louis, Mo.) is suspended in autoclaved water (BioWhittaker, Inc, Walkersville, Md.) at 5 mg/ml. A standard curve is generated from 500 micrograms/ml to 30 micrograms/ml in Lysis Buffer (see above). Standard curve and lysate samples are added at 5 microliters /well in duplicate to a polystyrene 96-well plate. Using the Sigma Plasma Hemoglobin Kit (Sigma Chemical Co., St. Louis, Mo.), TMB substrate is reconstituted in 50 mls room temperature acetic acid solution. One hundred microliters of substrate is added to each well, followed by 100 microliters/well of Hydrogen Peroxide Solution at room temperature. The plate is incubated at room temperature for 10 minutes.

Optical densities are determined spectrophotometrically at 600 nm in a 96-well plate reader, SpectraMax 250 Microplate Spectrophotometer System (Molecular Devices, Sunnyvale, Calif.). Background Lysis Buffer readings are subtracted from all wells. Total sample hemoglobin content is calculated according to the following equation:

Total Hemoglobin=(Sample Lysate Volume)×(Hemoglobin Concentration)

The average Total Hemoglobin of Matrigel samples without cells is subtracted from each Total Hemoglobin Matrigel sample with cells. Percent inhibition is calculated according to the following equation:

% Inhibition=

(Average Total Hemoglobin Drug-Treated Tumor Lysates) × 100 / (Average Total Hemoglobin Non-Treated Tumor Lysates)

The three preceding assays establish that the compounds of Formula I are active to inhibit VEGF receptor kinase activity and to inhibit angiogenesis.

In Vivo Assay of Antitumor Activity:

An in vivo assay of the inhibitory effect of the compounds on tumors (e.g., solid cancers) mediated by raf kinase can be performed as follows: CDI nu/nu mice (6-8 weeks old) are injected subcutaneously into the flank at 1×10⁶ cells with human colon adenocarcinoma cell line. The mice are dosed i.p., i.v. or p.o. at 10, 30, 100, or 300 mg/Kg beginning on approximately day 10, when tumor size is between 50-100 mg. Animals are dosed for 14 consecutive days; tumor size is monitored with calipers twice a week. The inhibitory effect of the compounds on p38, raf and VEGFR kinases and therefore on tumor growth (e.g., solid cancers) can further be demonstrated in vivo according to the technique of Monia et al. (*Nat. Med.* 1996, 2, 668-75).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A pharmaceutical composition comprising an effective amount of at least one compound of formula (I) and a physiologically acceptable carrier

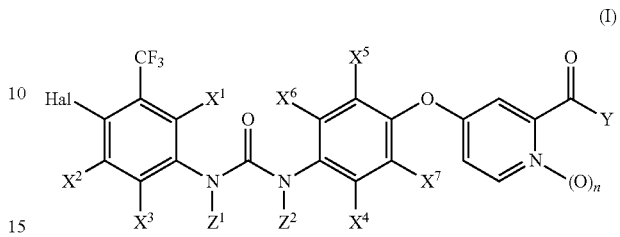

wherein,
Y is $OR^1$ or $NHR^2$,
Hal is chlorine or bromine,
$R^1$ is H or $C_1$-$C_6$ alkyl,
$R^2$ is H, OH, $CH_3$ or $CH_2OH$,
$Z^1$ and $Z^2$ are each H or OH, wherein only one of $Z^1$ or $Z^2$ can be OH,
$X^1$ to $X^7$ are each, independently, H, OH or $O(CO)C_1$-$C_4$ alkyl, and
n is 1,
or a salt thereof, or an isolated stereoisomer thereof.

2. A pharmaceutical composition of claim 1 wherein for the compound of formula (I), Y is $NHR^2$ and $R^2$ is H or $CH_3$.

3. A pharmaceutical composition of claim 1 wherein for the compound of formula (I),
a) $X^1$ to $X^7$ are each H, or
b) $Z^1$ and $Z^2$ are each H.

4. A pharmaceutical composition of claim 1 wherein for the compound of formula (I),
a) $X^1$ to $X^7$ are each H, or
b) $Z^1$ is H and $Z^2$ is OH or $Z^1$ is OH and $Z^2$ is H, or
c) $X^1$ to $X^7$ and $Z^1$ are each H and $Z^2$ is OH or
d) $X^1$ to $X^7$ and $Z^2$ are each H and $Z^1$ is OH.

5. A pharmaceutical composition of claim 1 wherein for the compound of formula (I), at least one of $X^1$ to $X^7$ is OH or $O(CO)C_1$-$C_4$ alkyl.

6. A pharmaceutical composition of claim 1 wherein for the compound of formula (I), Y is $NHR^2$ and $R^2$ is $CH_2OH$ or OH.

7. A pharmaceutical composition of claim 1 wherein for the compound of formula (I), Y is OH.

8. A pharmaceutical composition of claim 1 wherein for the compound of formula (I), $Z^1$ is H and $Z^2$ is OH or $Z^1$ is OH and $Z^2$ is H.

9. A pharmaceutical composition of claim 1 wherein for the compound of formula (I), $X^1$ to $X^7$ are each H.

10. A pharmaceutical composition of claim 1 wherein the compound of formula (I) is selected from the group consisting of:
4-{4-[({[4-chloro-3-(trifluoromethyl)phenyl]amino}carbonyl)amino]phenoxy}-N-methyl-2-pyridine carboxamide 1-oxide,
4-{4-[({[4-chloro-3-(trifluoromethyl)phenyl]amino}carbonyl)amino]phenoxy}-N-hydroxymethyl-2-pyridine carboxamide 1-oxide,
4-{4-[({[4-bromo-3-(trifluoromethyl)phenyl]amino}carbonyl)amino]phenoxy}-N-methyl-2-pyridine carboxamide 1-oxide,
4-{4-[({[4-bromo-3-(trifluoromethyl)phenyl]amino}carbonyl)amino]phenoxy}-N-hydroxymethyl-2-pyridine carboxamide 1-oxide, 4-{4-[({[4-chloro-3-(trifluoromethyl)phenyl]
amino}carbonyl)amino]phenoxy}-2-pyridine carboxamide 1-oxide, 4-{4-[({[4-bromo-3-(trifluoromethyl)phenyl]
amino}carbonyl)amino]phenoxy}-2-pyridine carboxamide 1-oxide, salts thereof and stereoisomers thereof.

11. A pharmaceutical composition of claim 1 wherein the compound of formula (I) is of formula (II), or a salt or stereoisomer thereof,

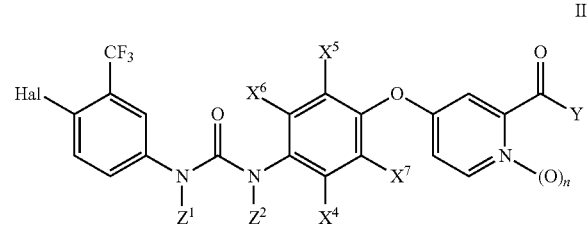

wherein,
Y is $OR^1$ or $NHR^2$,
Hal is chlorine or bromine,
$R^1$ is H or $C_1$-$C_6$ alkyl,
$R^2$ is H, OH, $CH_3$ or $CH_2OH$,
$Z^1$ and $Z^2$ are each H or OH, wherein only one of $Z^1$ or $Z^2$ is OH,
$X^4$ to $X^7$ are each, independently, H, OH or $O(CO)C_1$-$C_4$ alkyl, and
n is 1.

12. A pharmaceutical composition of claim 11, wherein in formula (II), $Z^1$ and $Z^2$ are each H.

13. A pharmaceutical composition of claim 12, wherein in formula (II), at least one of $X^4$ to $X^7$ is OH.

14. A pharmaceutical composition of claim 12, wherein in formula (II), Y is $NHR^2$ and $R^2$ is H or $CH_3$.

15. A pharmaceutical composition of claim 12, wherein in formula (II), Y is $NHR^2$ and $R^2$ is OH.

16. A pharmaceutical composition of claim 11, wherein in formula (II), at least one of $X^4$ to $X^7$ is OH.

17. A pharmaceutical composition of claim 1 wherein the compound of formula (I) is of formula (III), or a salt or isolated stereoisomer thereof,

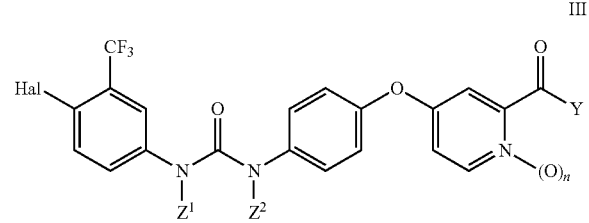

wherein,
Y is $OR^1$ or $NHR^2$,
Hal is chlorine or bromine,
$R^1$ is H or $C_1$-$C_6$ alkyl,
$R^2$ is H, OH, $CH_3$ or $CH_2OH$,
$Z^1$ and $Z^2$ are each H or OH, wherein only one of $Z^1$ or $Z^2$ can be OH, and
n is 1.

18. A pharmaceutical composition of claim 17, wherein in formula (III), n is 1 and $Z^1$ and $Z^2$ are each H.

19. A pharmaceutical composition of claim 18, wherein in formula (III), Y is $NHR^2$ and $R^2$ is H or $CH_3$.

20. A pharmaceutical composition of claim 17, wherein in formula (III), n is 0 and $Z^1$ is H and $Z^2$ is OH or $Z^1$ is OH and $Z^2$ is H.

21. A pharmaceutical composition of claim 20, wherein in formula (III), Y is $NHR^2$ and $R^2$ is H or $CH_3$.

22. A pharmaceutical composition of claim 17, wherein in formula (III), Y is OH.

23. A method of preparing compounds of formula (I) for a pharmaceutical composition

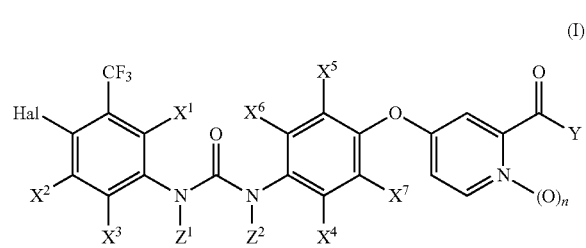

wherein,
Y is $OR^1$ or $NHR^2$,
Hal is chlorine or bromine,
$R^1$ is H or $C_1$-$C_6$ alkyl,
$R^2$ is H, OH, $CH_3$ or $CH_2OH$,
$Z^1$ and $Z^2$ are each H or OH, wherein only one of $Z^1$ or $Z^2$ can be OH,
$X^1$ to $X^7$ are each, independently, H, OH or $O(CO)C_1$-$C_4$ alkyl, and
n is 1
or a salt thereof, or an isolated stereoisomer thereof,
said method comprising oxidizing the pyridyl ring nitrogen to form the corresponding pyridine-1-oxide of:
4-{4-[({[4-chloro-3-(trifluoromethyl) phenyl] amino}carbonyl)amino]phenoxy}-N-methyl-2-pyridine carboxamide, 4-{4-[({[4-bromo-3-(trifluoromethyl) phenyl] amino}carbonyl)amino]phenoxy}-N-methyl-2-pyridine carboxamide, 4-{4-[({[4-chloro-3-trifluoromethyl)phenyl] amino}carbonyl)amino]phenoxy}-2-pyridine carboxamide, or 4-{4-[({[4-bromo-3-(trifluoromethyl)phenyl] amino}carbonyl)amino]phenoxy}-2-pyridine carboxamide, and optionally:

a) replacing one or more of the phenyl hydrogens at the positions represented by $X^1$ to $X^7$ with a hydroxyl group, b) hydroxylating the N-methyl amide into a hydroxymethyl amide or hydroxamic acid, c) demethylating the N-methyl amide into an unsubstituted amide, d) hydrolizing the N-methyl amide into a carboxylic acid, or e) providing a combination of two or more of a)-d); and isolating the resulting compound of formula (I).

24. A method of preparing compounds of formula (I),

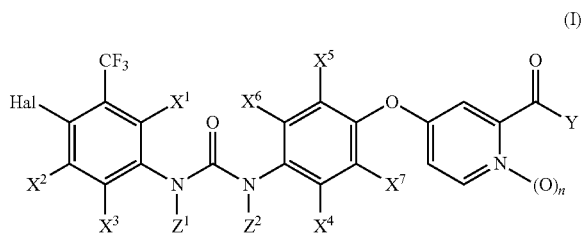

wherein,
Y is —NHOH,
Hal is chlorine or bromine,
$R^1$ is H or $C_1$-$C_6$ alkyl,
$Z^1$ and $Z^2$ are each H,
$X^1$ to $X^7$ are each, H, and
n is 0 or 1
or a salt thereof, or an isolated stereoisomer thereof,
said method comprising hydroxylating the N-methylamide to form the hydroxamic acid of
4-{4-[({[4-chloro-3-(trifluoromethyl)phenyl]amino}carbonyl)amino]phenoxy}-N-methyl-2-pyridine carboxamide,
4-{4-[({[4-bromo-3-(trifluoromethyl)phenyl]amino}carbonyl)amino]phenoxy}-N-methyl-2-pyridine carboxamide,
4-{4-[({[4-chloro-3-trifluoromethyl)phenyl]amino}carbonyl)amino]phenoxy}-2-pyridine carboxamide, or
4-{4-[({[4-bromo-3-(trifluoromethyl); and
isolating the resulting compound of formula (I).

25. A method as in claim 23 which prepares
4-{4-[({[4-chloro-3-(trifluoromethyl) phenyl]amino}carbonyl)amino]phenoxy}-N-methyl-2-pyridine carboxamide 1-oxide,
4-{4-[({[4-bromo-3-(trifluoromethyl)phenyl]amino}carbonyl)amino]phenoxy}-N-methyl-2-pyridine carboxamide 1-oxide,
4-{4-[({[4-chloro-3-(trifluoromethyl)phenyl]amino}carbonyl)amino]phenoxy}2-pyridine carboxamide 1-oxide,
4-{4-[({[4-bromo-3-(trifluoromethyl); and isolating the resulting compound of formula (I) phenyl]amino}carbonyl)amino]phenoxy}2-pyridine carboxamide 1-oxide, or a pharmaceutically acceptable salt of one of these oxides, or an isolated stereoisomer of one of these oxides.

26. A pharmaceutical composition comprising an effective amount of
4-{4-[({[4-chloro-3-(trifluoromethyl) phenyl]amino}carbonyl)amino]phenoxy}-N-methyl-2-pyridine carboxamide 1-oxide,
4-{4-[({[4-bromo-3-(trifluoromethyl)phenyl]amino}carbonyl)amino]phenoxy}-N-methyl-2-pyridine carboxamide 1-oxide,
4-{4-[({[4-chloro-3-(trifluoromethyl)phenyl]amino}carbonyl)amino]phenoxy}2-pyridine carboxamide 1-oxide,
4-{4-[({[4-bromo-3-(trifluoromethyl)phenyl]amino}carbonyl)amino]phenoxy}2-pyridine carboxamide 1-oxide or
a pharmaceutically acceptable salt of one of these oxides, an isolated stereoisomer of one of these oxides or a mixture thereof and a physiologically acceptable carrier.

27. A method of inhibiting p38 kinase in a cell by administering a pharmaceutical composition of claim 1 to said cell.

28. A method of inhibiting raf kinase in a cell comprising administering a pharmaceutical composition of claim 1 to said cell.

29. A method of inhibiting VEGFR2 kinase in a cell comprising administering a pharmaceutical composition of claim 1 to said cell.

30. A method of preparing N-[4-chloro-3-(trifluoromethyl)phenyl]-N'-{4-[2-(N-methylcarbamoyl)-1-oxo-(4-pyridyloxy)]phenyl}urea

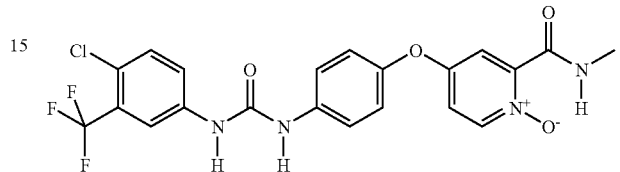

comprising chemically oxidizing N-[4-chloro-3-(trifluoromethyl)phenyl]-N'-{4-[2-(N-methylcarbamoyl)(4-pyridyloxy)]phenyl}urea in solution.

31. A method of preparing N-[4-chloro-3-(trifluoromethyl)phenyl]-N'-{4-[2-carbamoyl-1-oxo-(4-pyridyloxy)]phenyl}urea

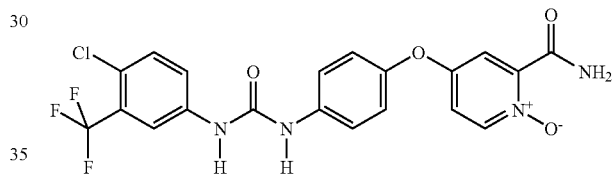

comprising chemically oxidizing N-[4-chloro-3-(trifluoromethyl)phenyl]-N'-{4-[2-carbamoyl-(4-pyridyloxy)]phenyl}urea in solution and isolating N-[4-chloro-3-(trifluoromethyl)phenyl]-N'-{4-[2-carbamoyl-1-oxo-(4-pyridyloxy)]phenyl} urea from said solution.

32. A pharmaceutical composition comprising an effective amount of at least one compound of formula (I) and a physiologically acceptable carrier,

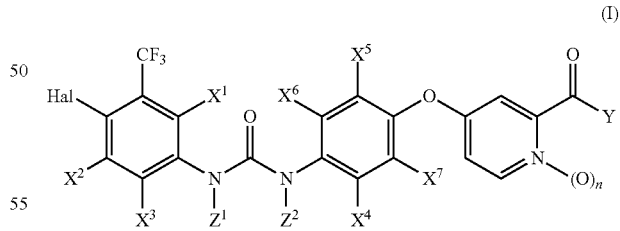

wherein,
Y is —NHOH,
Hal is chlorine or bromine,
$R^1$ is H or $C_1$-$C_6$ alkyl
$Z^1$ and $Z^2$ are each H,
$X^1$ to $X^7$ are each, H, and
n is 0 or 1
or a salt thereof, or an isolated stereoisomer thereof.

33. A pharmaceutical composition of claim 32, wherein n is 1 for formula I.

34. A pharmaceutical composition of claim 32, wherein n is 0 for formula I.

35. A pharmaceutical composition of claim 34, wherein $X^1$ to $X^7$ are each H for formula I.

36. A pharmaceutical composition comprising an effective amount of at least one compound of formula (I) and a physiologically acceptable carrier,

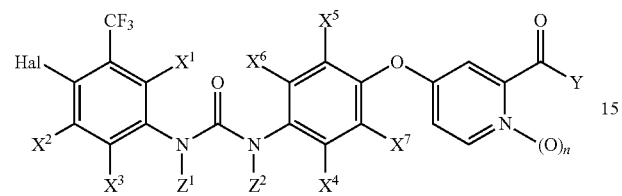
(I)

wherein,
Y is $OR^1$ or $NHR^2$,
Hal is chlorine or bromine,
$R^1$ is H or $C_1$-$C_6$ alkyl
$R^2$ is H, OH, $CH_3$ or $CH_2OH$,
$Z^1$ and $Z^2$ are each H or OH, wherein only one of $Z^1$ or $Z^2$ can be OH and $Z^1$ or $Z^2$ is OH,
$X^1$ to $X^7$ are each, independently, H, OH or $O(CO)C_1$-$C_4$ alkyl, and
n is 0 or 1
or a salt thereof, or an isolated stereoisomer thereof.

37. A pharmaceutical composition of claim 36, wherein $Z^1$ is H and $Z^2$ is OH or $Z^1$ is OH and $Z^2$ is H for formula I.

38. A pharmaceutical composition of claim 36, wherein at least one of $X^1$ to $X^7$ is OH or $O(CO)C_1$-$C_4$ alkyl for formula I.

39. A method of preparing compounds of formula (I)

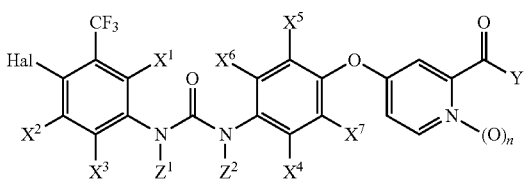
(I)

wherein,
Y is —NHOH,
Hal is chlorine or bromine,
$R^1$ is H or $C_1$-$C_6$ alkyl,
$Z^1$ and $Z^2$ are each H,
$X^1$ to $X^7$ are each, H, and
n is 0 or 1
or a salt thereof, or an isolated stereoisomer thereof
said method comprising hydroxylating the N-methylamide to form the hydroxamic acid of
4-{4-[({[4-chloro-3-(trifluoromethyl) phenyl]amino}carbonyl)amino]phenoxy}-N-methyl-2-pyridine carboxamide,
4-{4-[({[4-bromo-3-(trifluoromethyl) phenyl]amino}carbonyl)amino]phenoxy}-N-methyl-2-pyridine carboxamide,
4-{4-[({[4-chloro-3-trifluoromethyl)phenyl]amino}carbonyl)amino]phenoxy}-2-pyridine carboxamide, or
4-{4-[({[4-bromo-3-(trifluoromethyl) and isolating the compound of formula I.

* * * * *